US012622970B2

(12) United States Patent
Melican et al.

(10) Patent No.: US 12,622,970 B2
(45) Date of Patent: May 12, 2026

(54) PHOTOCURABLE REINFORCEMENT OF 3D PRINTED HYDROGEL OBJECTS

(71) Applicant: Lung Biotechnology PBC, Silver Spring, MD (US)

(72) Inventors: Mora Carolynne Melican, Weston, MA (US); Lara Murcin, Stratham, NH (US); Barbara Nsiah, Manchester, NH (US); Richmon Lin, Silver Spring, MD (US); Derek Morris, Bedford, NH (US); Lina Trigg, Silver Spring, MD (US); Luis Alvarez, Lexington, MA (US); Mohammadali Safavieh, Nashua, NH (US); Masoud Modaresifar, Manchester, NH (US); Kalyan Vydiam, Manchester, NH (US); Aman Kaur, Manchester, NH (US)

(73) Assignee: Lung Biotechnology PBC, Silver Spring, MD (US)

( * ) Notice: Subject to any disclaimer, the term of this patent is extended or adjusted under 35 U.S.C. 154(b) by 590 days.

(21) Appl. No.: 17/738,736

(22) Filed: May 6, 2022

(65) Prior Publication Data

US 2022/0354954 A1     Nov. 10, 2022

Related U.S. Application Data

(60) Provisional application No. 63/185,305, filed on May 6, 2021.

(51) Int. Cl.

| | |
|---|---|
| *A61K 47/32* | (2006.01) |
| *A61L 27/52* | (2006.01) |
| *A61P 9/10* | (2006.01) |
| *B29C 64/112* | (2017.01) |
| *B29C 64/264* | (2017.01) |
| *B29L 31/00* | (2006.01) |
| *B33Y 10/00* | (2015.01) |
| *B33Y 70/10* | (2020.01) |
| *B33Y 80/00* | (2015.01) |
| *B29K 105/00* | (2006.01) |
| *B29K 105/20* | (2006.01) |

(52) U.S. Cl.
CPC .............. *A61K 47/32* (2013.01); *A61L 27/52* (2013.01); *A61P 9/10* (2018.01); *B29C 64/112* (2017.08); *B29C 64/264* (2017.08); *B33Y 10/00* (2014.12); *B33Y 70/10* (2020.01); *B33Y 80/00* (2014.12); *B29K 2105/0061* (2013.01); *B29K 2105/206* (2013.01); *B29K 2995/0056* (2013.01); *B29L 2031/7532* (2013.01)

(58) Field of Classification Search
CPC ........ A61K 47/32; B33Y 10/00; B33Y 80/00; B33Y 70/10; B29C 64/264; B29C 64/112; A61P 9/10; A61L 27/52; B29K 2105/0061; B29K 2105/206; B29K 2995/0056; B29L 2031/7532
See application file for complete search history.

(56) References Cited

U.S. PATENT DOCUMENTS

| | | | |
|---|---|---|---|
| 5,645,581 A | 7/1997 | Zurbrugg | |
| 6,174,929 B1 | 1/2001 | Haehnle et al. | |
| 11,371,014 B2 | 6/2022 | Miller et al. | |
| 11,597,915 B2 | 3/2023 | Xu et al. | |
| 2008/0029392 A1 | 2/2008 | Makuska | |
| 2009/0011486 A1 | 1/2009 | Bettinger et al. | |
| 2010/0221304 A1* | 9/2010 | Tan ........................ | A61L 27/34 |
| | | | 977/702 |
| 2013/0029030 A1 | 1/2013 | Larsen | |
| 2014/0335496 A1 | 11/2014 | Grego et al. | |
| 2017/0307598 A1 | 10/2017 | Skardal et al. | |
| 2017/0354758 A1 | 12/2017 | Deng et al. | |
| 2018/0002658 A1 | 1/2018 | Miller et al. | |
| 2018/0243481 A1* | 8/2018 | Martin .................. | A61L 31/148 |
| 2020/0040306 A1 | 2/2020 | Xu et al. | |
| 2020/0179563 A1 | 6/2020 | Bagley et al. | |
| 2020/0324021 A1 | 10/2020 | Van Belleghem et al. | |
| 2020/0339925 A1 | 10/2020 | Miller et al. | |
| 2020/0347167 A1 | 11/2020 | Alli et al. | |
| 2021/0069378 A1 | 3/2021 | Nelson et al. | |

FOREIGN PATENT DOCUMENTS

| | | | |
|---|---|---|---|
| CN | 105688279 A | | 6/2016 |
| DE | 10 2019 132 211 B3 | | 4/2021 |
| EP | 0 466 105 A2 | | 1/1992 |
| EP | 3 514 228 A1 | | 7/2019 |
| JP | 2018-036524 A | | 3/2018 |
| WO | WO-2005/105172 A1 | | 11/2005 |
| WO | WO-2016/154070 A1 | | 9/2016 |
| WO | WO-2017/031167 A1 | | 2/2017 |
| WO | WO-2017/040156 A1 | | 3/2017 |
| WO | WO-2017/066507 A1 | | 4/2017 |
| WO | WO-2017/210298 A1 | | 12/2017 |
| WO | WO-2018/187372 A2 | | 10/2018 |
| WO | WO-2019/195256 A1 | | 10/2019 |

(Continued)

OTHER PUBLICATIONS

U.S. Appl. No. 17/738,686, filed May 6, 2022, Melican et al.
U.S. Appl. No. 17/738,694, filed May 6, 2022, Kaur et al.
U.S. Appl. No. 17/738,698, filed May 6, 2022, King et al.
U.S. Appl. No. 17/738,764, filed May 6, 2022, Kaur et al.
U.S. Appl. No. 17/738,833, filed May 6, 2022, Modaresifar et al.
Akentjew et al., "Rapid fabrication of reinforced and cell-laden vascular grafts structurally inspired by human coronary arteries," Nature Communications, Dec. 1, 2019, 10(1):1-15.
Ali et al., "A Photo-Crosslinkable Kidney ECM-Derived Bioink Accelerates Renal Tissue Formation," Advanced Healthcare Materials, Apr. 1, 2019, 8(7):e1800992, 10 pages.

(Continued)

*Primary Examiner* — Michael P Cohen
(74) *Attorney, Agent, or Firm* — Foley & Lardner LLP

(57) ABSTRACT

The present disclosure provides reinforced hydrogel structures, methods of reinforcing hydrogel structures, and methods of treating ischemic disorders using the reinforced hydrogel structures.

16 Claims, 33 Drawing Sheets

(56) References Cited

FOREIGN PATENT DOCUMENTS

| | | |
|---|---|---|
| WO | WO-2019/226710 A8 | 11/2019 |
| WO | WO-2020/028720 A1 | 2/2020 |
| WO | WO-2020/182987 A1 | 9/2020 |

OTHER PUBLICATIONS

Baek et al., "In situ assembly of the collagen-polyacrylamide interpenetrating network hydrogel: Enabling decoupled control of stiffness and degree of swelling," European Polymer Journal, Nov. 1, 2015, 72:413-422.

Bilisik et al., "3D fabrics for technical textile applications," in Non-woven Fabrics, Chapter 4, Intech, 2016, 81-141.

Calo et al., "Biomedical applications of hydrogels: A review of patents and commercial products," European Polymer Journal, Apr. 2015, 65:252-267.

Fukao et al., "Hydrogels toughened by biominerals providing energy-dissipative sacrificial bonds," J. Mater. Chem. B, 2020, 8:5184-5188.

Galliger et al., "3D bioprinting for lungs and hollow organs," Translational Research, May 14, 2019, 211:19-34.

Han, Hai-Chao, "Twisted Blood Vessels: Symptoms, Etiology and Biomechanical Mechanisms," J. Vasc. Res., May 2012 (online Mar. 14, 2012), 49(3):185-197.

Koobatian et al., "Surgical Technique for the Implantation of Tissue Engineered Vascular Grafts and Subsequent In Vivo Monitoring," J. Vis. Exp., Apr. 3, 2015, (98):52354, 1-11.

Marga et al., "Toward engineering functional organ modules by additive manufacturing," Biofabrication, Jun. 1, 2012, 4(2):022001, 13 pages.

Pashneh-Tala et al., "The Tissue-Engineered Vascular Graft-Past, Present and Future," Tissue Engineering: Part B, 2016 (online Oct. 7, 2015), 22(1):68-100.

Weigel et al., "Photopolymer formulations for uSL printing of hydrogel microstructures as swellable functional elements," Progress in Biomedical Optics and Imaging, SPIR—International Society for Optical Engineering, Mar. 5, 2021, 11637:116370A-1-116370A13.

Zhu et al., "Bioactive modification of poly(ethylene glycol) hydrogels for tissue engineering," Biomaterials, Jun. 1, 2010, 31(17):4639-4656.

Fan et al., "Bio-printing cell-laden Matrigel-agarose constructs," Journal of Biomaterials Applications, 2016, 31(5):684-692.

Grigoryan et al., "Multivascular networks and functional intravascular topologies within biocompatible hydrogels," Science, May 3, 2019, 364(6439):458-464, with Supplementary materials (39 pages).

Huh et al., "Reconstituting Organ-Level Lung Functions on a Chip," Science, Jun. 25, 2010, 328(5986):1662-1668.

Kim et al., "Bio-ink Materials for 3D Bio-printing," Journal of International Society for Simulation Surgery, 2016, 3(2):49-57.

Ma et al., "A Novel Method for Preparing Poly(vinyl alcohol) Hydrogels: Preparation, Characterization, and Application," Industrial & Engineering Chemistry Research, Jun. 21, 2017, 56:7971-7976.

MilliporeSigma. https://www.sigmaaldrich.com/deepweb/assets/sigmaaldrich/marketing/global/images/technical-documents/articles/analytical-chemistry/purification/solvent-miscibility-table/solvent-miscibility-table.png. (Year: 2024).

Scarritt et al., "Re-endothelialization of rat lung scaffolds through passive, gravity-driven seeding of segment-specific pulmonary endothelial cells," Journal of Tissue Engineering and Regenerative Medicine, 2018 (May 7, 2017), 12:e786-e806.

Seo et al., "Characterization of bioactive RGD peptide immobilized onto poly(acrylic acid) thin films by plasma polymerization," Applied Surface Science, 2010, 257:596-602.

Stratesteffen et al., "GelMA-collagen blends enable drop-on-demand 3D printability and promote angiogenesis," Biofabrication, 2017, 9:045002, 1-12.

Vila et al., "Hydrogel co-networks of gelatine methacrylate and poly(ethylene glycol) diacrylate sustain 3D functional in vitro models of intestinal mucosa," Biofabrication, 2020, 12:025008, 1-16.

Wang et al., "Development of a Photo-Crosslinking, Biodegradable GelMA/PEGDA Hydrogel for Guided Bone Regeneration Materials," Materials, Aug. 3, 2018, 11:1345, 1-12.

Yin et al., "3D Bioprinting of Low-Concentration Cell-Laden Gelatin Methacrylate (GelMA) Bioinks with a Two-Step Cross-linking Strategy," ACS Applied Materials & Interfaces, Feb. 6, 2018, 10:6849-6857.

Yue et al., "Synthesis, properties, and biomedical applications of gelatin methacryloyl (GelMA) hydrogels," Biomaterials, 2015, 73:254-271.

Zhuang et al., "Layer-by-layer ultraviolet assisted extrusion-based (UAE) bioprinting of hydrogel constructs with high aspect ratio for soft tissue engineering applications," PLoS ONE, 2019, 14(6):e0216776, 1-21.

Ha et al., "Conductive GelMA-Collagen-AgNW Blended Hydrogel for Smart Actuator," Polymers, Apr. 9, 2021, 13:1217, 1-10.

* cited by examiner

B

A

F

E

Vicryl Woven Mesh

Vicryl Knitted Mesh

B

A

A

B

C

Gray-Scaling Introduction of Mesh Reinforcement 48 mJ/cm² No Mesh 48 mJ/cm² Mesh 98.4 m/cm²

48 mJ/cm² Mesh 165.6 m/cm²

B

A

Figure 25
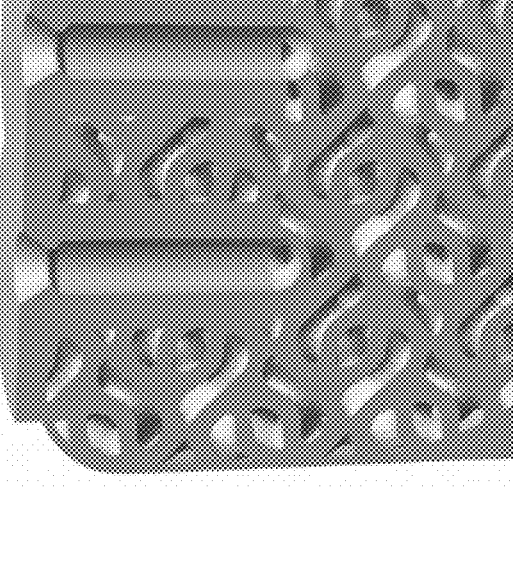
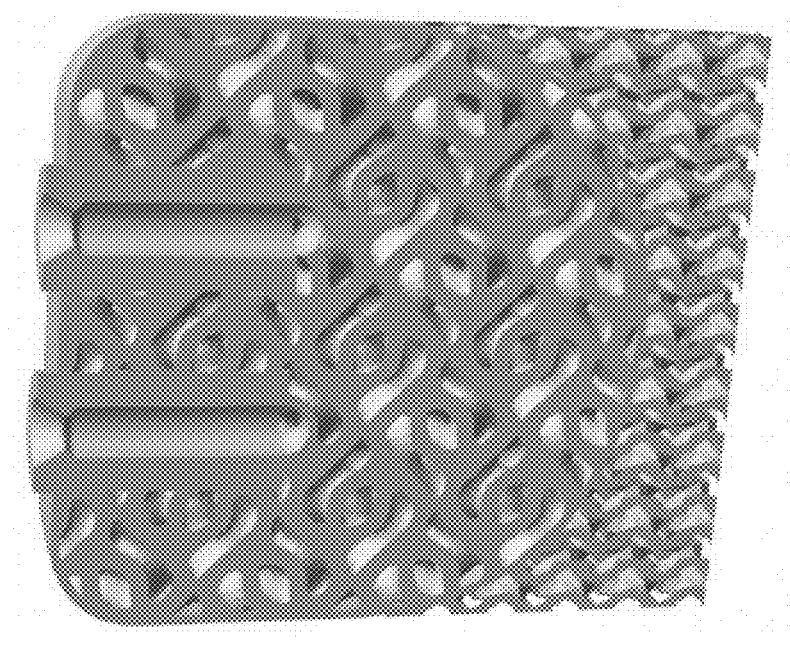

PHOTOCURABLE REINFORCEMENT OF 3D PRINTED HYDROGEL OBJECTS

CROSS-REFERENCE TO RELATED APPLICATIONS

This application claims priority to U.S. Provisional Application No. 63/185,305, filed May 6, 2021, the entire contents of which are incorporated herein by reference.

BACKGROUND

Three-dimensional (3D) hydrogel structures have increasing uses for various biomedical applications. However, the mechanical properties of a hydrogel construct can often lead to problems with the durability of these constructs.

In the past, those in the field altered the mechanical properties by forming a "skin" on the surface of a hydrogel structure in a process that was tedious, time consuming, and hard to reproduce. In addition, the "skin" was sometimes fragile itself. For example, Raghavan et al., used a complex methodology employing concentric molds to create a hollow cylindrical structure. The delicate materials are difficult to remove from the molds, and in a second step, the surface of the tube is treated with an agent that causes polymer chains to crosslink in the gel structure. It is difficult to control the depth of this treatment.

Others in the field have uses additives to elicit a chemical reaction throughout the hydrogel that changes the mechanical properties. This has several distinct disadvantages. One is that the beneficial properties of soft hydrogel scaffolds interacting with the cells is lost when the material properties are changed like this. A second disadvantage of this approach is the need to add an additional material type to the system, which may have a negative effect on cellular response. This more complex implant will also take longer to get regulatory approval. For example, Gaharwar has been able to increase a hydrogel's stiffness by 10 times and its toughness by 20 times through a process in which he adds a small amount of spherical, magnetic nanoparticles to the collagen-based hydrogels. Others toughen hydrogels by adding ceramic particles, such as Fukao (*J. Mater. Chem. B,* 2020, 8, 5184-5188). This approach would only work in limited applications in which the presence of a ceramic would not be detrimental to the healing of the tissue.

Accordingly, there exists a need in the art to improve the mechanical properties of hydrogel structures in a manner that is repeatable and that does not create an overly complex device, and/or does not drastically alter the beneficial properties of soft hydrogel scaffolds.

SUMMARY

Some embodiments of the present disclosure are directed to a method of reinforcing a three-dimensional (3D) hydrogel structure, comprising contacting a mesh immersed in uncured photocurable bioink with the structure, and irradiating the mesh immersed in uncured photocurable bioink, thereby adhering it to the 3D hydrogel structure.

Some embodiments of the present disclosure are directed to a composition comprising a three-dimensional (3D) hydrogel structure and a layer comprising a mesh immersed in a photocurable or photocured ink, and wherein the layer comprising a mesh immersed in a photocurable or photocured ink is in contact with the structure.

Some embodiments of the present disclosure are directed to a method of treating ischemic disease in a subject in need thereof, the method comprising implanting the reinforced structure or composition disclosed herein.

BRIEF DESCRIPTION OF THE DRAWINGS

FIG. 2A: Formlabs through tube with plug and flare. FIG. 2B: Luer lock standard fitting with zip tie. FIG. 2C: Formlabs fixture reinforced with cohesive bandage, steri-strips, and glue/paper (sticks and rips tube). FIG. 2D: Glue and filter paper reinforcement of tube. FIG. 2E: Technical drawing of the construct shown in FIGS. 2A, 2B & 2C. FIG. 2F: Tube fixed to bottom of container to maintain horizontal configuration and eliminate tube-bend induced by tube buoyancy. FIG. 2G: Tube apparatus to eliminate glue usage. FIG. 2H: Tube with enhanced mounting ends. FIG. 2I: Tube with enhanced mounting ends R3=inner diameter and R6=outer diameter.

FIG. 3A: Clamped into a vice, a jig for mounting membrane for suture pull out test with u-shaped port for suture placement (FIG. 3B) in membrane inserted into the jig. FIG. 3C: submerged reinforced hydrogel. FIG. 3D: Jig with sandpaper support for gripping to exert force for suture pull out testing. FIG. 3E: Suture types, $\frac{3}{8}^{th}$ circle was used in the suture pull out test.

FIG. 4A: Purse string suture technique. FIG. 4B: Connector attached to native vessel via purse string suture shown in FIG. 4B. FIG. 4C: Mesh on tube being photocured. FIG. 4D: Mesh to be place around tube and photocured. FIG. 4E: Mesh placed over tube and photocured. FIG. 4F: Saw-like top edge can cut through photocured ink.

FIG. 5A: Tubular hydrogel reinforced with mesh and sutured to Gore-Tex™ (Flagstaff, AZ) smooth walled vascular graft. FIG. 5B: Vicryl woven mesh reinforced tube (left panel) with magnified mesh (right panel). FIG. 5C: Vicryl knitted mesh reinforced tube (left panel) with magnified mesh (right panel).

FIG. 10A: Mesh reinforced tubes implanted into porcine. FIG. 10B: Tubes attached to native rabbit tissue in vivo. FIG. 10C: Loop of 3D printed graft material indicated with arrow coupled to PA of rabbit.

FIG. 12A: Shows PA which is isolated, clamped, and cut. FIG. 12B shows polyethylene spacer (central longer tube) glued end to end onto 3D printed tubes (arrows overlayed on 3D printed tubes). FIG. 12C: The animal is anesthetized, pulmonary artery is cut, the device shown in FIG. 12B is sutured at each end to each respective end of the cut PA.

FIG. 15A: Interface of tubing and printed tube shown with arrow. Blunt tip needle slid into the interior of the hyrodgel tube. Secured with cyanoacrylate glue. FIG. 15B: Both ends are attached directly to a blunt tip needle, perfused with DPBS+India Ink, submerged in 1×PBS, then pumped at 0.1 mL per stroke/–25 strokes/minute=2.5 mL/min and left to cycle overnight.

FIG. 20A shows a representative 602n curve, B is tensile pull of porcine carotid artery. FIG. 20B shows tensile testing. FIG. 20C shows the two graphs overlaid of 20A and 20B. The overlay is important because it shows an order of magnitude difference between hydrogel alone and native tissue.

FIG. 25: 3D airway prints according to the Examples.

DETAILED DESCRIPTION

Figure 1:
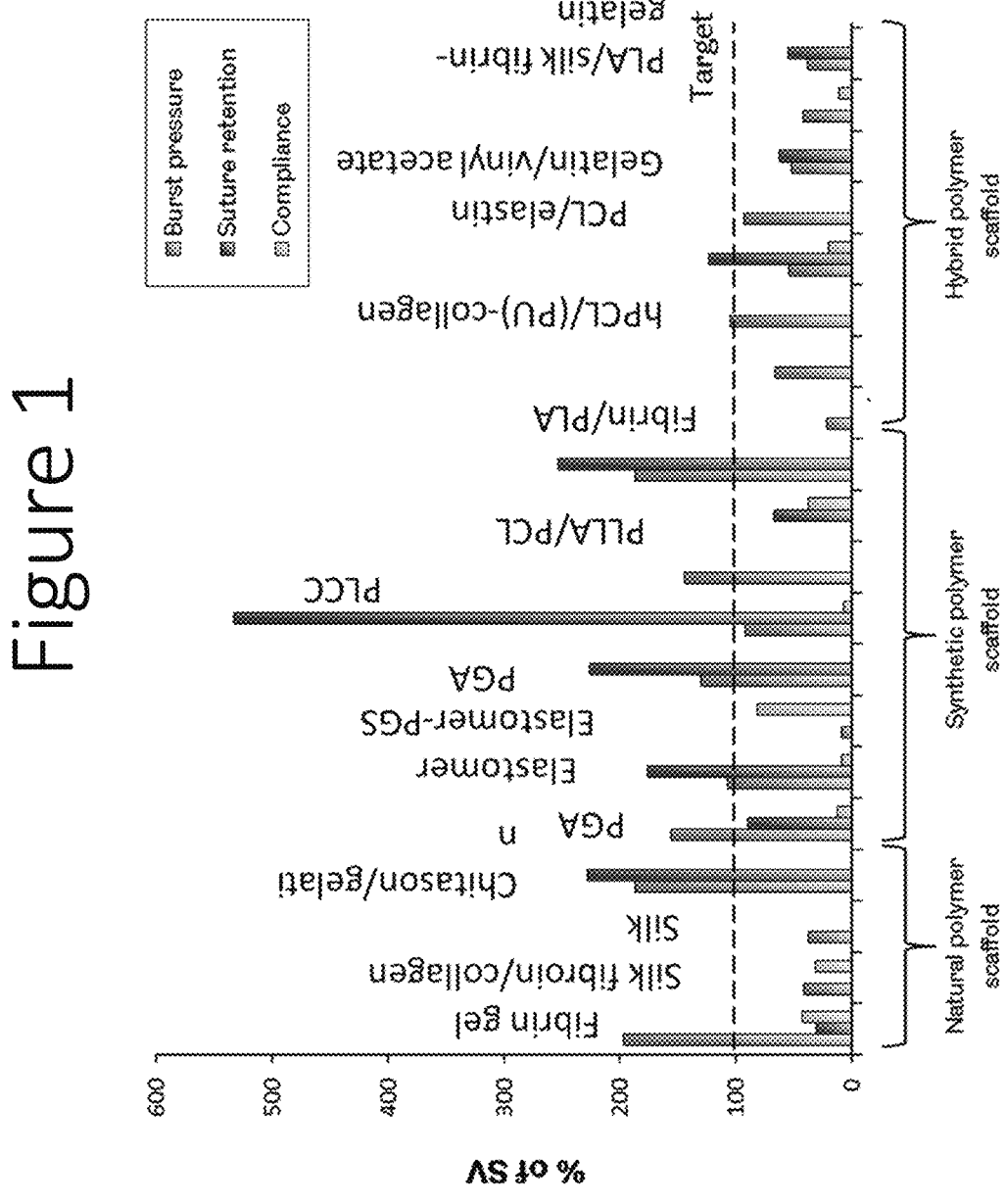
FIG. 1: Exemplary graph showing the mechanical properties of the tissue engineered vascular graft (TEVG) (burst pressure, suture retention, and compliance) compared with saphenous vein (SV). Burst pressure: 2134 mmHg=284 kPa; Suture retention strength: 1.92 N; and Compliance: 25.6%/100 mmHg. See Pashneh-Tala et al., *Tissue Engineering*: Part B, Volume 22, pg. 68, Number 1, 2016.
Figure 2A:
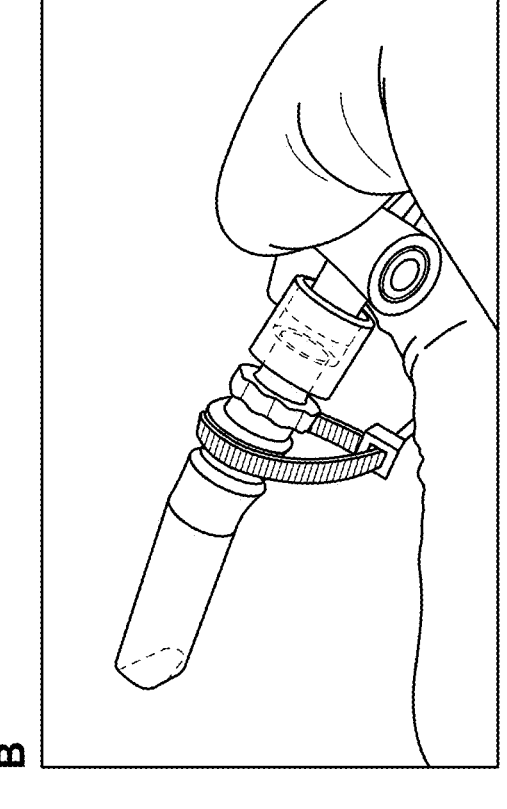
FIGS. 2A-2I: Experimental apparatus for burst test development on hydrogel tubes.
Figure 2B:
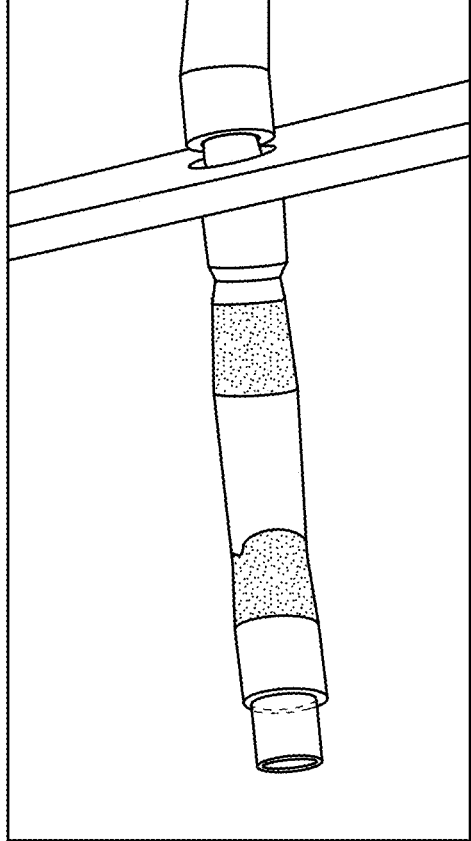
Figure 2C:
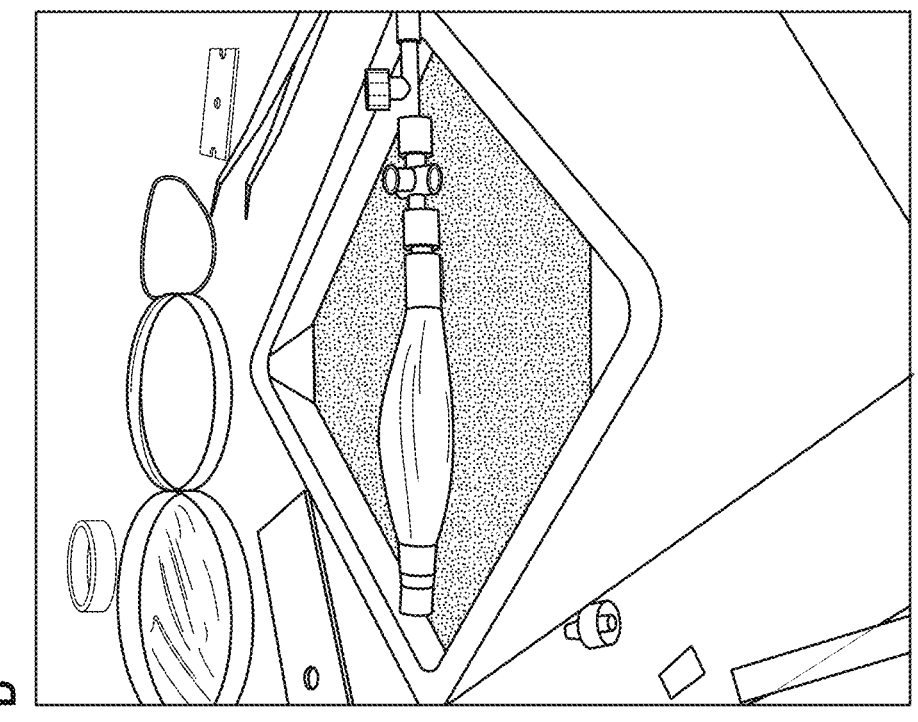
Figure 2D:
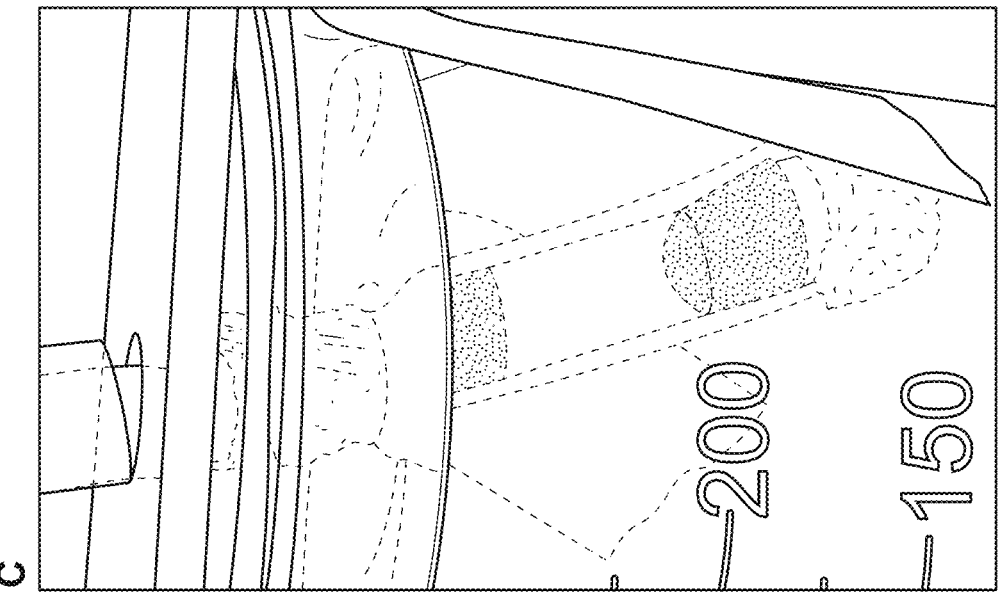
Figure 2E:
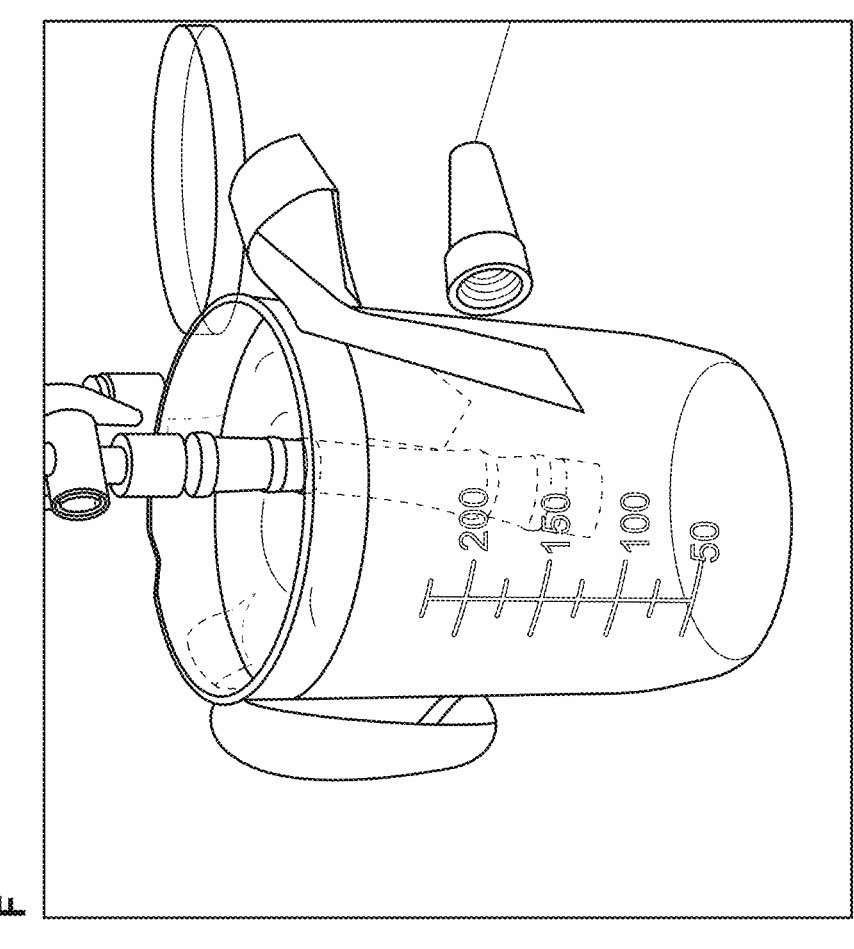
Figure 2F:
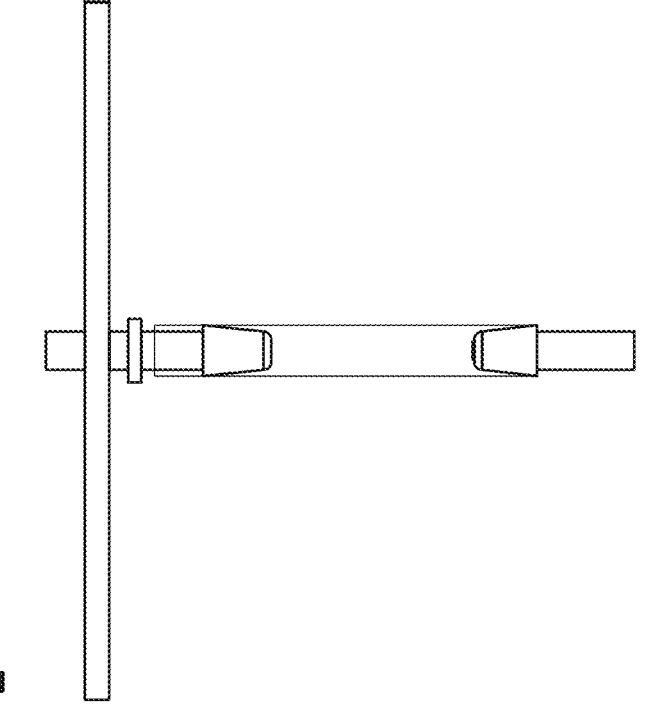
Figures 2G, 2H, 2I:
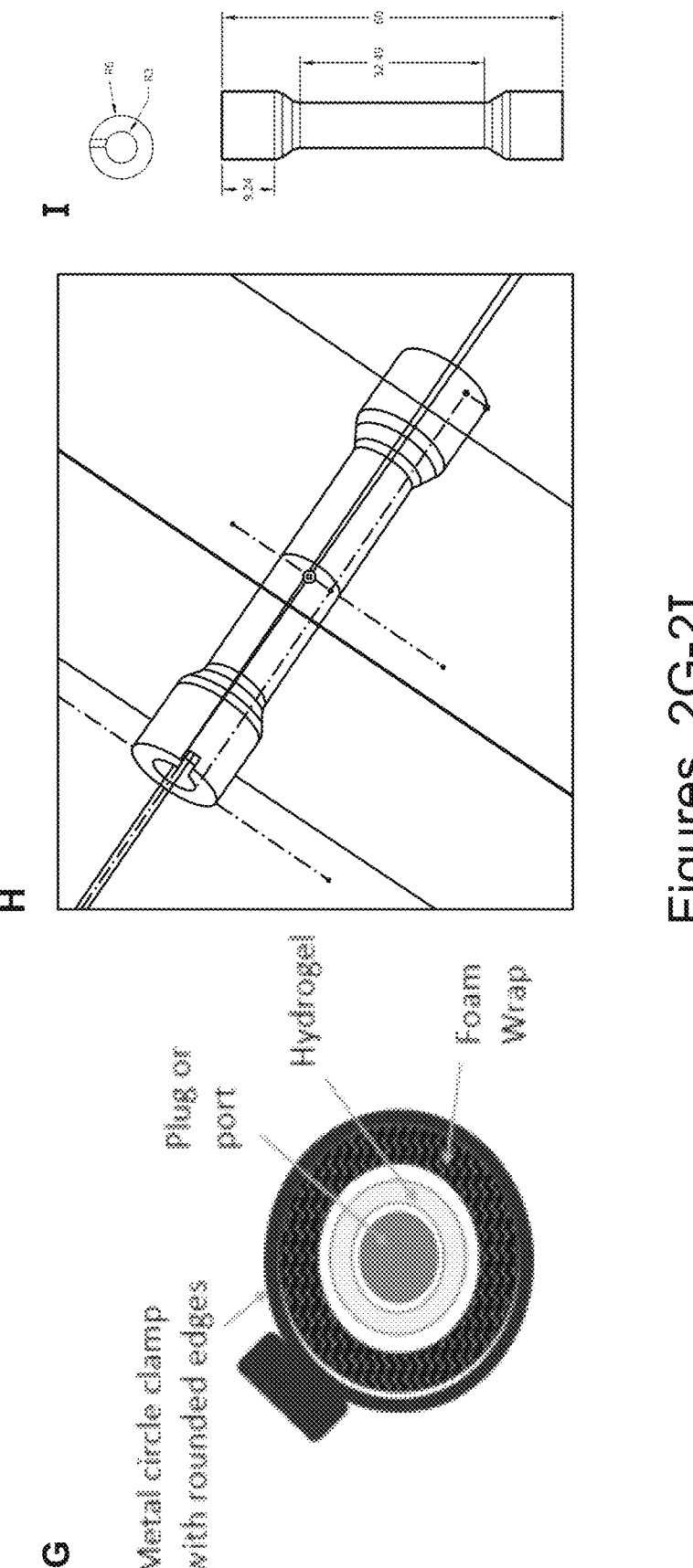
Figures 3A, 3B, 3C, 3D:
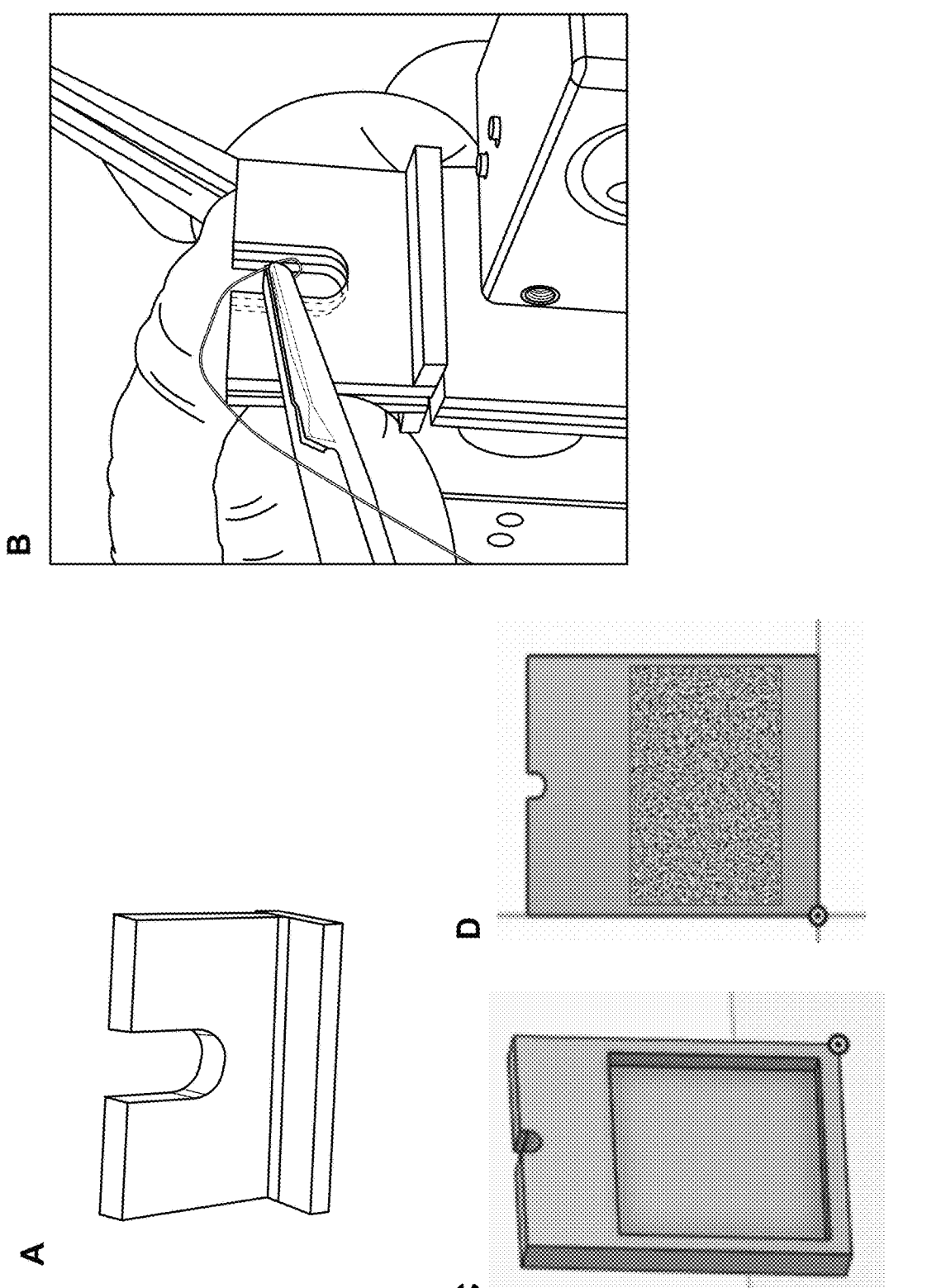
FIGS. 3A-3E: Suture pull out test apparatus as described in Example 8.
Figure 3E:
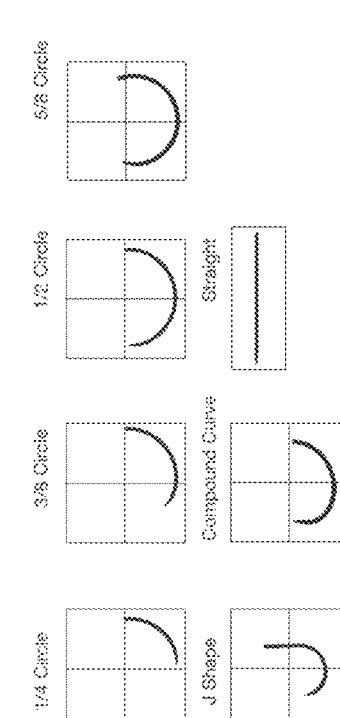

The present disclosure includes embodiments directed to methods of reinforcing a three-dimensional (3D) hydrogel structure. Additional embodiments include a reinforced three-dimensional (3D) hydrogel structure and methods of treating ischemic disease in a subject in need thereof, the method comprising implanting a reinforced three-dimensional (3D) hydrogel structure.

As used herein, the singular forms "a," "an," and "the" include plural referents unless the content clearly dictates otherwise. For example, reference to "a cell" includes a combination of two or more cells, and the like.

As used herein, "weight percent" (also expressed as "wt %"), refers to the percent of one or more components relative to the total mass of the composition. Thus, a composition with a mass of 100 grams comprising 10 grams of Compound A has a weight percent of 10% for Compound A. As used herein, weight percent is used synonymously with mass percent.

Various patterns of fabric and weaves thereof in embodiments herein are defined in Bilisik et al., "3D Fabrics for Technical Textile Applications" Submitted: Mar. 15, 2015 Reviewed: Jul. 14, 2015 Published: Mar. 24, 2016, DOI: 10.5772/61224. These definitions of textile terminology are well known in the art: Knit mesh is comprised of a single fiber that is formed into interlocking loops to produce a series of openings. Woven meshes are made up of multiple fibers that cross each other to create a series of openings. A felt otherwise known as a non-woven, is a matt of individual fibers that are interlocked by tangling, or the application of heat, chemicals, pressure, or a combination. A bonded non-woven is a felt that contains a second material that bonds the intersections of the tangled fibers of the matt. A braided flat or tubular mesh is a construct that has a circular rather than flat cross-section, that is produced by interlacing three or more fibers. Velcro is a series of loop and hooks, when pressed together becomes entangled via the catching of the hooks in the loops. A lace is a fabric with a web-like structure produced by twisting, braiding, looping, interlacing, or a combination.

All references cited herein are hereby incorporated by reference in their entireties. The definitions are provided to facilitate understanding of certain terms used throughout this specification. Technical and scientific terms used herein have the meanings commonly understood by one of ordinary skill in the art, unless otherwise defined. Any suitable materials and/or methodologies known to those of ordinary skill in the art can be utilized in carrying out the methods described herein.

The term "administering" or "implanting" as used herein includes prescribing for administration, as well as actually administering, and includes physically administering to the subject being treated by another, for example, a surgeon.

As used herein "subject" or "patient" or "individual" refers to any subject, patient, or individual and the terms are used interchangeably herein. In this regard, the terms "subject," "patient," and "individual" includes mammals, and, in particular humans.

As used herein, the term "comprising" or "comprises" is intended to mean that the compositions and methods include the recited elements, but not excluding others. "Consisting essentially of" when used to define compositions and methods, shall mean excluding other elements of any essential significance to the combination for the stated purpose. Thus, a composition consisting essentially of the elements as defined herein would not exclude other materials or steps that do not materially affect the basic and novel characteristic(s) of the claimed invention. "Consisting of" shall mean excluding more than trace elements of other ingredients and substantial method steps. Embodiments defined by each of these transition terms are within the scope of this invention. When an embodiment is defined by one of these terms (e.g., "comprising"), it should be understood that this disclosure also includes alternative embodiments, such as "consisting essentially of" and "consisting of" for said embodiment.

"Substantially" or "essentially" means nearly totally or completely, for instance, 95%, 96%, 97%, 98%, 99%, or greater of some given quantity.

The term "about" will be understood by persons of ordinary skill in the art and will vary to some extent depending upon the context in which it is used. If there are uses of the term which are not clear to persons of ordinary skill in the art given the context in which it is used, "about" will mean up to plus or minus 10% of the particular term. For example, in some embodiments, it will mean plus or minus 5% of the particular term. Certain ranges are presented herein with numerical values being preceded by the term "about." The term "about" is used herein to provide literal support for the exact number that it precedes, as well as a number that is near to or approximately the number that the term precedes. In determining whether a number is near to or approximately a specifically recited number, the near or approximating unrecited number may be a number, which, in the context in which it is presented, provides the substantial equivalent of the specifically recited number.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges and are also encompassed within the invention, subject to any specifically excluded limit in the stated range. Where the stated range includes one or both of the limits, ranges excluding either or both of those included limits are also included in the disclosure.

As used herein, the term "treatment" or "treating" means any treatment of a disease or condition or associated disorder, in a patient, including:

Inhibiting or preventing the disease or condition, that is, arresting or suppressing the development of clinical symptoms, such as neurological deficits resulting from cerebral ischemia, also included within "treatment" is provision of neuroprotection; and/or relieving the disease or condition that is, causing the regression of clinical symptoms (e.g., increasing neurological performance or reducing neurological deficits).

As used herein, the term "gray-scaling" or "voxel printing" refers to in situ processing of a mesh design into the object. The parameters are altered and can print in a way that alters the curing at the specific 3D point in space, or the voxel in the resulting object. Each voxel can be printed with completely different parameters, and thus the object can be printed from the same material but varying properties.

The present application incorporates by reference in their entirety each of the following documents: (a) U.S. provisional application No. 63/185,293 filed May 6, 2021 titled "USE OF FUNCTIONALIZED AND NON-FUNCTIONALIZED ECMS, ECM FRAGMENTS, PEPTIDES AND BIOACTIVE COMPONENTS TO CREATE CELL ADHESIVE 3D PRINTED OBJECTS" and U.S. non-provisional and/or PCT application(s) under the same title filed on May 6, 2022; (b) U.S. provisional application No. 63/185,302 filed May 6, 2021 titled "MODIFIED 3D-PRINTED OBJECTS AND THEIR USES" and U.S. non-provisional and/or PCT application(s) under the same title filed on May 6, 2022; (c) U.S. provisional application No. 63/185,300 filed May 6, 2021 titled "CONTROLLING THE SIZE OF 3D PRINTING HYDROGEL OBJECTS USING HYDROPHILIC MONOMERS, HYDROPHOBIC MONOMERS, AND CROSSLINKERS" and U.S. non-provisional and/or PCT application(s) under the same title filed on May 6, 2022; (d) U.S. provisional application No. 63/185,299 filed May 6, 2021 titled "ADDITIVE MANUFACTURING OF HYDROGEL TUBES FOR BIOMEDICAL APPLICATIONS" and U.S. non-provisional and/or PCT application(s) under the same title filed on May 6, 2022; (e) U.S. provisional application No. 63/185,298 filed May 6, 2021 titled "MICROPHYSIOLOGICAL 3-D PRINTING AND ITS APPLICATIONS" and U.S. non-provisional and/or PCT application(s) under the same title filed on May 6, 2022.

Methods of Reinforcing a Three-Dimensional (3D) Hydrogel Structure and Compositions Comprising the Same Certain embodiments of the present disclosure relate to a method of reinforcing a three-dimensional (3D) hydrogel structure, comprising contacting a reinforcement scaffold immersed in uncured curable bioink with the structure, and irradiating the reinforcement scaffold immersed in uncured curable bioink, thereby adhering it to the 3D hydrogel structure. In some embodiments, the curable bioink is photocurable, e.g., via UV irradiation at a particular wavelength.

In another aspect, the disclosure provides a composition comprising a three-dimensional (3D) hydrogel structure and a layer comprising a mesh immersed in a photocurable or photocured ink, and wherein the layer comprising a mesh immersed in a photocurable or photocured ink is in contact with the structure.

The 3D shape of the hydrogel structure is not particularly limited, and may be in a shape of a tube, or substantially the same shape, size, and/or has the same relative dimensions of an organ or a fragment of an organ.

In some embodiments, the 3D shape of the hydrogel structure is substantially the same shape, size, and/or has the same relative dimensions of an organ or a fragment of an organ. In certain embodiments, the organ or fragment of the organ comprises a vessel, trachea, bronchi, esophagus, ureter, renal tubule, bile duct, renal duct, bile duct, hepatic duct, nerve conduit, CSF shunt, lung, kidney, heart, liver, spleen, brain, gallbladder, stomach, pancreas, bladder, lymph vessel, skeletal bone, cartilage, skin, intestine, a muscle, larynx, or pharynx. In additional embodiments, the vessel shape comprises a pulmonary artery, renal artery, coronary artery, peripheral artery, pulmonary vein, or renal vein. In certain embodiments, the structure comprises a hemodialysis graft. Other embodiments include where the structure is substantially is the shape of a lung lobe, lung, airway tree of a lung, lung vasculature, or a combination thereof. In some embodiments, the reinforcement comprises maintaining air-flow or blood (or fluid) flow through the structure when an external pressure is applied to the structure.

In some embodiments, the 3D shape of the hydrogel structure is in a shape of a tube. In certain embodiments, the structure comprises a hollow tube comprising a first end and a second end. In some embodiments, the structure comprises a first subtube and a second subtube, each having a first end, wherein the structure comprises the first subtube and second subtube connected to each other at their first ends to form a joint of the tube, and wherein the reinforcement scaffold contacts the joint. In some embodiments, the reinforcement scaffold is contacting the first and/or second end of the tube.

Certain embodiments include a distance between the first end and the second end of the tube that defines a tube length, and wherein the reinforcement scaffold is contacting a sublength of the tube defined by a distance from the first end and/or second end to a point on the tube that is X % of the tube length away from said first end and/or second end in contact with the reinforcement scaffold, wherein X is selected from about 0.01% to about 0.1%, about 0.1% to about 1%, about 1% to about 5%, about 5% to about 10%, about 10% to about 20%, about 20% to about 30%, about 30% to about 40%, or about 40% to about 50%. In some embodiments, the sublength comprises about 1 mm to about 2.5 mm, about 2.5 mm to about 5 mm, about 5 mm to about 7.5 mm, about 7.5 mm to about 1 cm, or about 1 cm to about 2.5 cm.

The reinforcement scaffold is not particularly limited. Exemplary reinforcement scaffolds of the present disclosure include knitted meshes, woven meshes, non-woven constructs (e.g., felts), bonded non-woven constructs, braided tubular fabrics, braided flat fabrics, thin films, perforated thin films, velcro, and lace (or other weave that does not fray at the edge when cut). Additional materials include those described in Bilisik, K., et al, "3D fabrics for technical textile applications," Non-woven Fabrics. Intech (2016): 81-141, which is incorporated herein by reference. In certain embodiments, the reinforcement scaffold is a mesh. In some embodiments, the reinforcement scaffold is substantially planar and comprises a thickness of about 0.1 μm to about 2 mm. For instance, embodiments of the reinforcement scaffold thickness include about 0.1 μm, 0.2 μm, 0.3 μm, 0.4 μm, 0.5 μm, 0.6 μm, 0.7 μm, 0.8 μm, 0.9 μm, 1 μm, 2 μm, 3 μm, 4 μm, 5 μm, 6 μm, 7 μm, 8 μm, 9 μm, 10 μm, 15 μm, 20 μm, 50 μm, 100 μm, 150 μm, 200 μm, 250 μm, 500 μm, 750 μm, 1 mm, 1.1 mm, 1.2 mm, 1.3 mm, 1.4 mm, 1.5 mm, 1.6 mm, 1.7 mm, 1.8 mm, 1.9 mm, 2 mm, and ranges therein between.

Non-limiting examples of reinforcement scaffold materials of this disclosure include polyglactin (Vicryl®), polyglycolic acid (PGA), polylactic acid (PLA), monofilament propylene (e.g., SoftMesh, Parietex-TET, TIGR, Marlex), Dacron, Teflon, polytetraflourethylene, polycaprolactone mesh, PGA/PCL, PGA/PLA/PCL and combinations thereof. In a preferred embodiment, 95/5 PCL/PGA mesh is used. This material has a preferred degradable time of approximately 9-12 months. In some embodiments, the material is made from two or more types of fiber. For example, when the material is made from two or more types of fiber, at least one of the fibers can degrade more quickly resulting in a reinforcement scaffold that becomes less dense over time, e.g., for enhanced tissue ingrowth. An example is a composite that is a PLA mesh with fibers of PGA incorporated (woven or knitted or braided). Another example is a composite with PCL fibers that has PGA fibers incorporated.

The placement of the reinforcement scaffold can be adjusted to improve mechanical properties of some or all of the structure. In some embodiments, the reinforcement scaffold spirals around the tube sublength or encircles the tube on an inside and/or outside surface of the tube. In some embodiments, the reinforcement scaffold contacts both the inside and outside surface of the tube. In other embodiments, the reinforcement scaffold wraps from the inside surface of the tube to the outside surface of the tube, around a tube edge at the first end and/or second end of the tube.

The present disclosure also includes reinforcing a site of the structure that is to be sutured, is cracked, is torn, is weakened, is subject to mechanical stress, is thinned, is infected, and/or is diseased. In some embodiments, the reinforcement comprises kink resistance and/or collapse prevention of the tube. In some embodiments, reinforcement is at a suture site of the structure and increases suture pull out force of the structure by about 2.5 times to about 5 times, about 5 times to about 7.5 times, about 7.5 times to about 10 times, about 10 times to about 15 times, or by greater than about 15 times versus an non-reinforced suture site of the structure.

Additional embodiments include reinforcement at a site of the structure for connectivity to biological tissue or a graft material.

The three-dimensional (3D) hydrogel structure is not particularly limited, and can be, e.g., a composite structure made of one or more different polymerized monomers. Hydrogel materials that may be used in the invention may be known to those having ordinary skill in the art, as are methods of making the same. For example, a hydrogel as described in Caló et al., *European Polymer Journal* Volume 65, April 2015, Pages 252-267 may be used. In some embodiments, the hydrogel structure comprises a polymerized (meth)acrylate and/or (meth)acrylamide hydrogel. In some embodiments, the structure comprises a polymer comprising polymerized poly(ethylene glycol) di(meth)acrylate, polymerized poly(ethylene glycol) di(meth)acrylamide, polymerized poly(ethylene glycol) (meth)acrylate/(methacrylamide), poly(ethylene glycol)-block-poly(ε-caprolactone), polycaprolactone, polyvinyl alcohol, gelatin, methylcellulose, hydroxyethyl methyl cellulose, hydroxypropyl methyl cellulose, polyethylene oxide, polyacrylamides, polyacrylic acid, polymethacrylic acid, salts of polyacrylic acid, salts of polymethacrylic acid, poly(2-hydroxyethyl methacrylate), polylactic acid, polyglycolic acid, polyvinylalcohol, polyanhydrides such as poly(methacrylic) anhydride, poly(acrylic) anhydride, polysebasic anhydride, collagen, poly(hyaluronic acid), hyaluronic acid-containing polymers and copolymers, polypeptides, dextran, dextran sulfate, chitosan, chitin, agarose gels, fibrin gels, soy-derived hydrogels, alginate-based hydrogels, poly(sodium alginate), hydroxypropyl acrylate (HPA), lithium phenyl-2,4,6-trimethylbenzoylphosphinate (LAP) and combinations thereof. In some embodiments, the Mw of the hydrogel polymer is about 400 Da, 500 Da, 600 Da, 700 Da, 800 Da, 900 Da, 1000 Da, 1100 Da, 1200 Da, 1300 Da, 1400 Da, 1500 Da, 1600 Da, 1700 Da, 1800 Da, 1900 Da, 2000 Da, 2100 Da, 2200 Da, 2300 Da, 2400 Da, 2500 Da, 2600 Da, 2700 Da, 2800 Da, 2900 Da, 3000 Da, 3100 Da, 3200 Da, 3300 Da, 3400 Da, 3500 Da, 3600 Da, 3700 Da, 3800 Da, 3900 Da, 4000 Da, 4100 Da, 4200 Da, 4300 Da, 4400 Da, 4500 Da, 4600 Da, 4700 Da, 4800 Da, 4900 Da, 5000 Da, 5100 Da, 5200 Da, 5300 Da, 5400 Da, 5500 Da, 5600 Da, 5700 Da, 5800 Da, 5900 Da, 6000 Da, 6100 Da, 6200 Da, 6300 Da, 6400 Da, 6500 Da, 7000 Da, 7500 Da, 8000 Da, 8500 Da, 9000 Da, 9500 Da, 10000 Da, 15000 Da, or 20000 Da.

In some embodiments, hydrogel comprises a cross linked polymer. In some embodiments, the polymer is about 0% to about 10%, about 10% to about 20%, about 20% to about 30%, about 30% to about 40%, about 40% to about 50%, about 50% to about 60%, about 60% to about 70%, about 70% to about 80%, about 80% to about 90%, or about 90% to about 100% cross-linked, based on the percentage of the cross-linkable moieties in the polymer. Cross linkable moieties may include, for example, (meth)acrylate groups.

The curable bioink is not particularly limited. In some embodiments, the bioink is the same or similar in composition to the monomers used in the three-dimensional (3D) hydrogel structure. In some embodiments, the curable bioink is a photocurable ink, e.g., an ink that can be photocured in the UV spectrum range 100-400 nm. Possible inks include a photoinitiator and/or dye that reacts and absorbs light at the range of 100-400 nm. Photoinitiators, may include, for example, benzophenone, phenyl bis (2,4,6-trimethylbenzoyl) phosphine oxide (BAPO), 2-hydroxy-2-methyl-1-phenyl-propan-1-one, 2-hydroxy-4'-(2-hydroxethoxy)-2-methylpropiophenone, 2,2'-azobis[2-methyl-n-(2-hydroxyethyl) propionamide], 2,2-dimethoxy-2-phenylacetophenone, diphenyl(2,4,6-trimethylbenzoyl)phosphine oxide, lithium phenyl(2,4,6-trimethylbenzoyl) phosphinate (LAP), and ethyl (2,4,6-trimethylbenzoyl)phenylphosphinate.

In certain embodiments, the hydrogel comprises a 3D-printed object. The skilled artisan would appreciate the methods of printing known in the art, and non-limiting examples include selective laser sintering (SLS) method, a fused deposition modeling (FDM) method, a 3D inkjet printing method, a digital light processing (DLP) method, and a stereolithography method. In the fused deposition modeling (FDM) method, the inks are deposited by an extrusion head, which follows a tool-path defined by a CAD file. The materials are deposited in layers as fine as 20 μm thick, and the part is built from the bottom up, one layer at a time. Some 3D printers based on the fused deposition modeling method are equipped with dual print nozzle heads that can extrude two different materials, one being a building material and the other being a support, such as a pillar, material. The support material can be washed with water.

3D inkjet printing is effectively optimized for speed, low cost, high resolution, and ease-of-use, making it suitable for visualizing during the conceptual stages of engineering design through to early-stage functional testing. Complicated 3D articles in the ink-jet printing method are produced from ink compositions by jetting followed by UV/Vis light. The photo-curable ink in the ink-jet printing process may be jetted through several nozzles on the building platform with a pattern defined by a CAD file.

An efficient technology among 3D printing technologies is a digital light process (DLP) method or stereolithography (SLA). In a 3D printer using the DLP or SLA method, the ink material is layered on a vat or spread on a sheet, and a predetermined area or surface of the ink is exposed to ultraviolet-visible (UV/Vis) light that is controlled by a digital micro-mirror device or rotating mirror. In the DLP method, additional layers are repeatedly or continuously laid and each layer is cured until a desired 3D article is formed. The SLA method is different from the DLP method in that ink is solidified by a line of radiation beam. Other methods of 3D printing may be found in 3D Printing Techniques and Processes by Michael Degnan, December 2017, Cavendish Square Publishing, LLC, the disclosure of which is hereby incorporated by reference.

Compositions of the disclosure may be packaged together with or included in a kit along with instructions or a package insert. Such instructions or package inserts may address recommended storage conditions, such as time, temperature and light, taking into account the shelf-life of the composition. Such kits may also include instructions for medical implantation into a patient and follow-up care for the patient. Such instructions or package inserts may also address the particular advantages of the composition, such as the ease of storage for formulations that may require use in the field, outside of controlled hospital, clinic or office conditions. In one aspect, the instructions may comprise visual aid/pictorial and/or written directions to an administrator, fabricator, or recipient of the composition.

In one aspect, the kit may comprise one or more compositions as disclosed herein, wherein the composition may be sealed within a first protective packaging, or a second protective packaging, or a third protective packaging, that protects the physical integrity of the product. One or more of the first, second, or third protective packaging may comprise a foil pouch. The kit may further comprise instructions for use of the device. In one aspect, the kit contains two or more devices.

Methods of Treating Ischemic Disease

In one aspect, a method of treating ischemic disease in a subject in need thereof is provided, the method comprising implanting the reinforced structure produced by the method of any embodiment herein comprising contacting a mesh immersed in uncured photocurable bioink with the structure, and irradiating the mesh immersed in uncured photocurable bioink, thereby adhering it to the 3D hydrogel structure Tortuous or kinked arteries and veins are commonly observed in humans and animals. While mild tortuosity is asymptomatic, severe tortuosity can lead to ischemic attack in distal organs. Clinical observations have linked tortuous arteries and veins with aging, atherosclerosis, hypertension, genetic defects and diabetes mellitus. Han et al., *J. Vasc. Res.* 2012 May; 49(3): 185-197. The implantation of reinforced tubes of the disclosure into vessels having the potential to kink or beginning to kink, may treat and/or prevent ischemic disorders from occurring or progressing.

The ischemic disease may comprise a cerebral or general ischemic disorder. In one embodiment, the cerebral or general ischemic disorder is selected from microangiopathy, intrapartum cerebral ischemia, cerebral ischemia during/after cardiac arrest or resuscitation, cerebral ischemia due to intraoperative problems, cerebral ischemia during carotid surgery, chronic cerebral ischemia due to stenosis of blood-supplying arteries to the brain, sinus thrombosis or thrombosis of cerebral veins, cerebral vessel malformations, diabetic retinopathy, high blood pressure, high cholesterol, myocardial infarction, cardiac insufficiency, cardiac failure, congestive heart failure, myocarditis, pericarditis, perimyocarditis, coronary heart disease, angina pectoris, congenital heart disease, shock, ischemia of extremities, stenosis of renal arteries, diabetic retinopathy, thrombosis associated with malaria, artificial heart valves, anemias, hypersplenic syndrome, emphysema, lung fibrosis, erectile dysfunction, or pulmonary edema.

For example, the methods of the disclosure may show an improvement in one or more characteristics of the cerebral or general ischemic disorder as measured by a medically recognized scale. The improvement may be, for example, about 5%, about 10%, about 15%, about 20%, about 25%, about 30%, about 35%, about 40%, about 45%, about 50%, about 55%, about 60%, about 65%, about 70%, about 75%, about 80%, about 85%, about 90%, about 95%, or about 100%.

Medically recognized scales or techniques to measure improvement include, for example, cholesterol test, high-sensitivity C-reactive protein test, lipoprotein (a), plasma ceramides, natriuretic peptides, low density lipoprotein cholesterol, high density lipoprotein cholesterol, triglycerides, electrocardiogram (EKG), Holter monitor, stress test, echocardiogram, positron emission tomography (PET), thallium scans, myocardial perfusion scans, implantable loop recorder, tilt table test, electrophysiology study, coronary angiogram, magnetic resonance imaging, magnetic resonance angiography, cardiac CT scan, and event recorder.

Methods of surgical implantation of synthetic vessels or tissue engineered vascular grafts, including the reinforced tubes disclosed herein, are disclosed in the present examples and known to those having ordinary skill in the art. Koobatian et al., *J Vis Exp.* 2015; (98): 52354. Methods known in the art to surgically implant TEVGs may be modified by those having ordinary skill in the art as disclosed herein, namely, to reinforce said vessel as described herein before suturing the TEVG to native vessel or tissue.

In some embodiments, the subject is a human or an animal. In some embodiments, the subject is selected from a human, equine, canine, feline, bovine, porcine, ayes, or reptile.

Embodiments described herein are further illustrated by, though in no way limited to, the following working examples.

EXAMPLES

Example 1: Method of Making Reinforced Pleura Using Meshes

The objective of this entry is to document the effect of applying mesh on the pleura in our scaffold. The ventilation experiments show the effectiveness of the process. To try this mesh, Applicant used one of the prints of FIG. 25 which leaked in pleura during the ventilation test. Then the VKML 90/10 PLGA was applied around the scaffold by and the mesh was covered by 602N. 602N tubes contain the following components as shown in Table 1

TABLE 1

| 602N Components | |
| --- | --- |
| Component | Wt (%) |
| PEGDA-6k | 3-10 |
| LAP | 0-5 |
| UV386a | 0.01-0.1 |
| HBA | 5-15 |
| Water | 80-95 |

*Legend: hydroxypropyl acrylate (HPA), lithium phenyl-2,4,6-trimethylbenzoylphosphinate (LAP), poly(ethylene glycol) diacrylate (PEGDA), hydroxy-4-butyl-acrylate (HBA)

A hand held UV light with 385 wavelength was applied for 1 minute on every part of the print until it polymerized on the surface. The covered piece then was placed into buffer for one hour before it assembled into a bioreactor and connected to ventilator.

Example 2: Preparation of 6 cm Length Tubes-Mesh Ends for Porcine Use

This experiment established the procedure for attachment of reinforcing mesh to hydrogel tubes and curing using light. The steps conducted were as follows:
1. Trim tube
2. Wipe end for application well with kimwipe. This removes excess buffer and prevents barrier layer between new formulation and original object.
3. Dip end in formulation or apply drop with bulb pipette.
4. Apply end of fabric and tack in place with the flashlight.
5. Wrap around, continue to dip and cure until secured.
6. The UV source was mounted in ring stand.
7. Tube was very close to source with the lamp suspended from the ring stand.
8. Tack on a small region of the end of the mesh. Slowly rotate adding formulation as needed.
9. When the whole circumference of the tube is covered by mesh trim excess with surgical scissors.
10. Continue to coat the graft with drips of the 602N formulation and rotating to cure. It helps to place the tube on a plastic rod so that fingers are not exposed to the UV light. Occasionally pinch the mesh down to the surface of the tube with forceps to ensure tight binding.
11. Check for gaps in adherence by bending the tube at the interface with the mesh. If nothing is observed and slight pulling doesn't dislodge the mesh, drop tube into the bath of PBS to rinse out any uncured material.

Example 3: Suture Pull Assay

Figure 6:
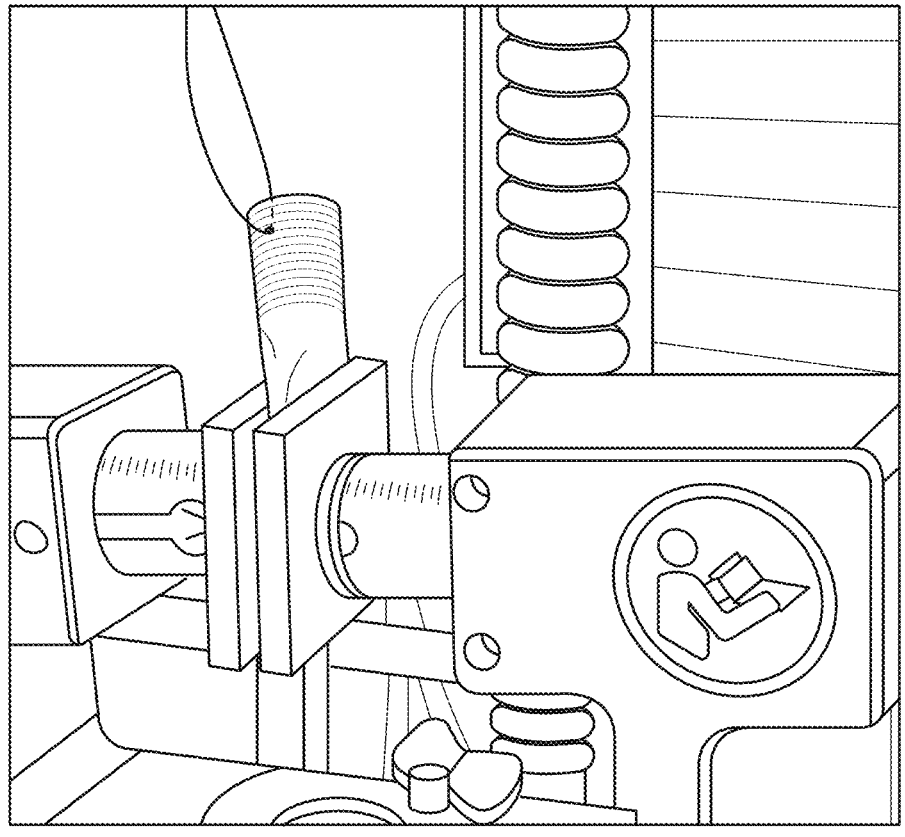
FIG. 6: Apparatus for mesh reinforced tube suture pull experiment of Example 3. Tube is in vice with suture thread through mesh at end of tube.
Figure 7:
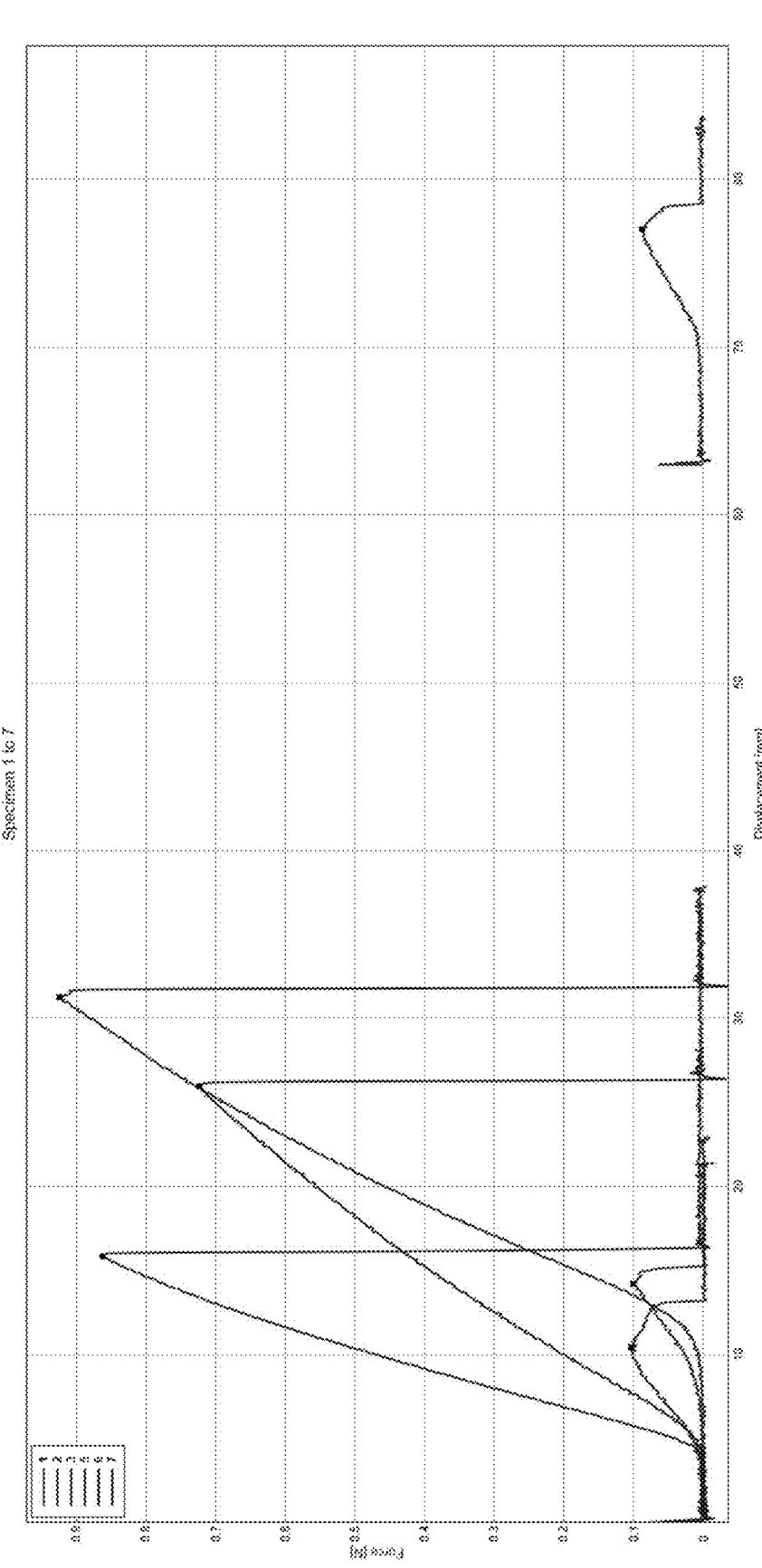
FIG. 7: Graphical data showing force required for pull-out for 7 different suture pull out experiments of Example 3 on reinforced tubes (lines 5-7) and naked non-reinforced tubes (lines 1-3). Y axis shows force exerted on tube and X axis shows distance of displacement to affect pull-out

Method: Three short tubes were prepped for testing on Instron apparatus (FIG. 6) for suture pull out values. The sections of the tube that were trimmed off had mesh applied at one end in same manner as the 6 cm tubes described in Example 2. The experiment compared tubes with no mesh to reinforced-mesh tubes. All were from same 10 cm long batch.

A 3 mm bite was marked with ink and then the needle was passed through that target mark and thread pulled through using slender forceps. The suture secured to the top grip of the apparatus.

Figure 8:
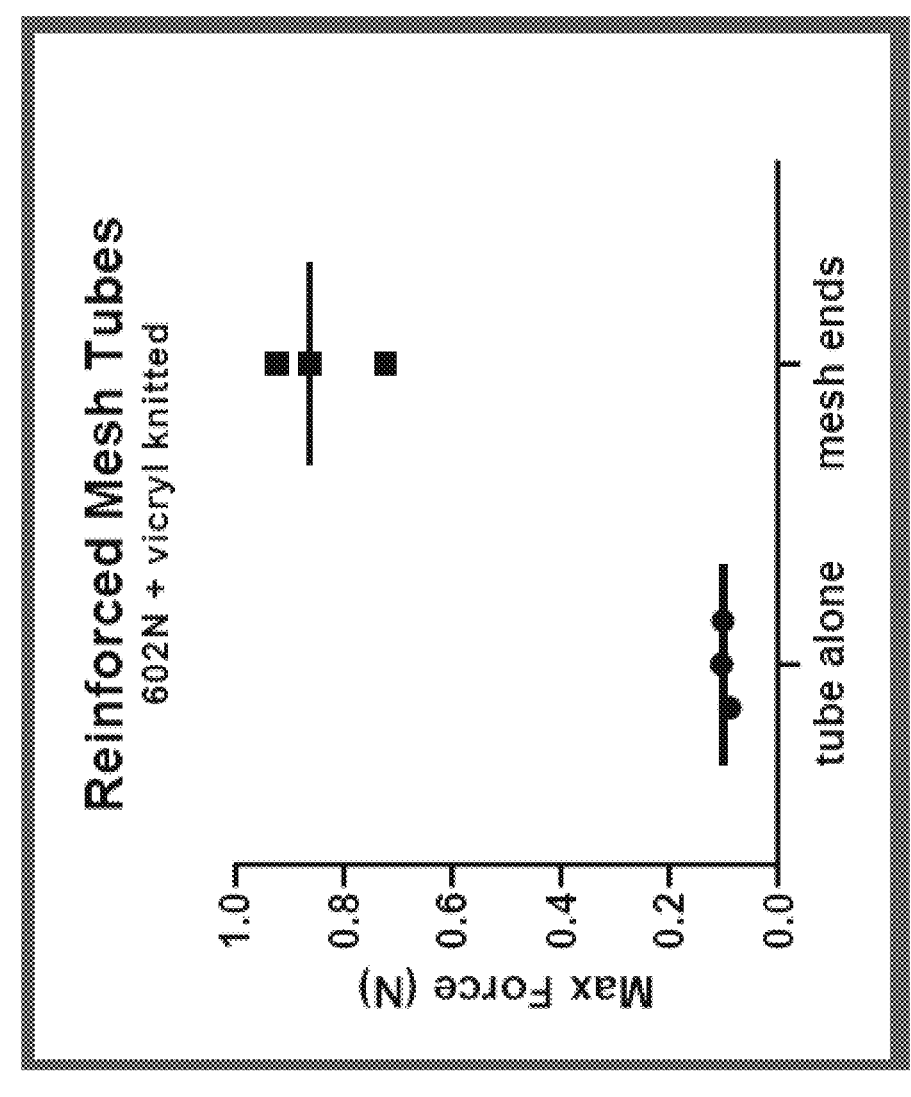
FIG. 8: Pull out force experimental results of Example 3 of mesh reinforced tube vs. tube without mesh. Reinforced tubular hydrogels demonstrate an 8-fold increase in suture pull out force compared to unmodified tubular hydrogels.

Results: All of the reinforced tubes ripped the region of mesh off of the body of the tube. No cases of the suture pulling through the mesh itself were observed. Non-reinforced tubes were cut through with ease by the suture, requiring approx. 8-10× less force to cause the pull-out (FIG. 8).

Example 4: Hydrogel Sutured with No Leaks

The objective of this experiment was to suture a reinforced hydrogel tube to a PTFE graft tube and inject fluid into the joined tubes and demonstrate the absence of leaks.

Figures 5A, 5B, 5C:
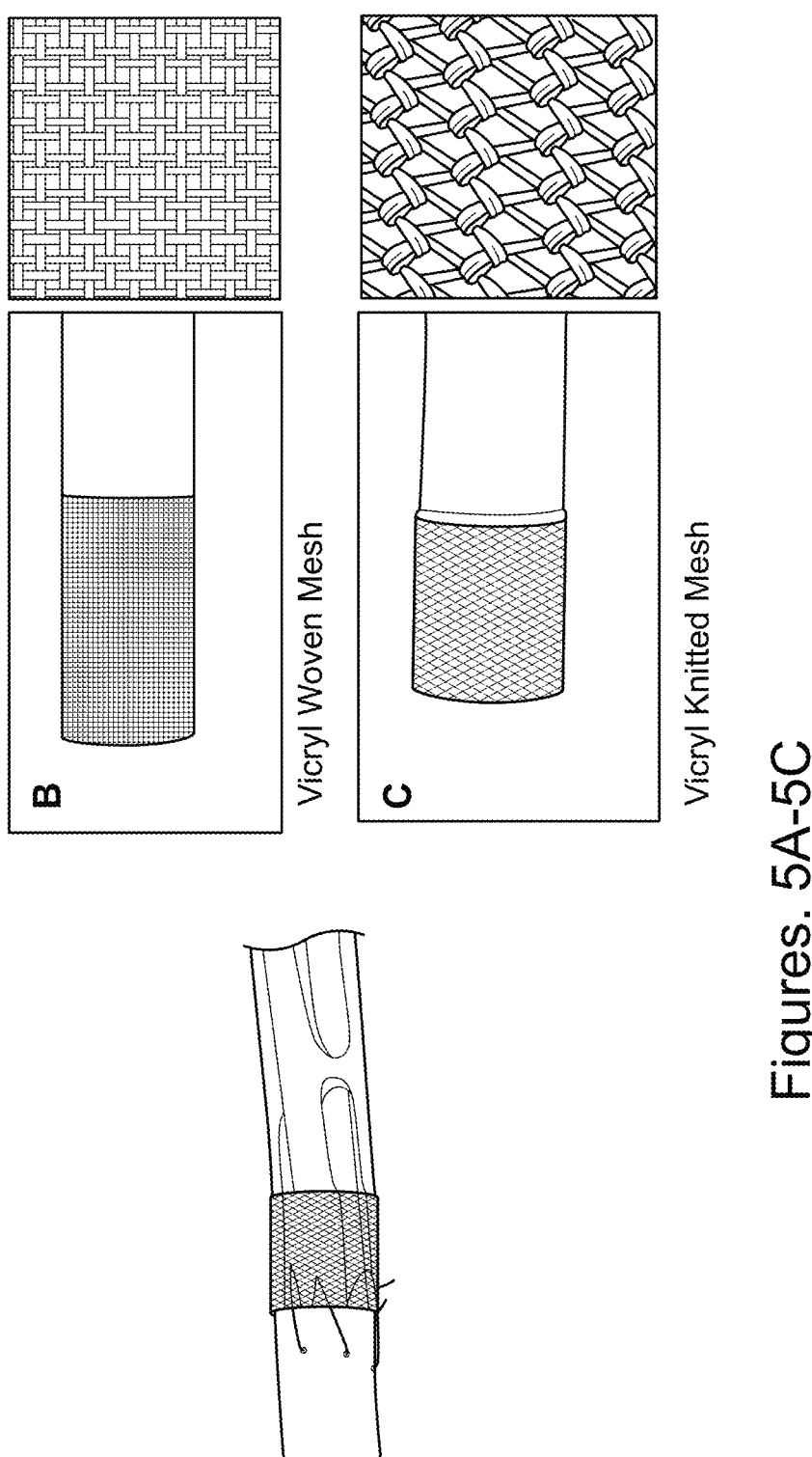
FIGS. 5A-5C: Vicryl™ (Somerville, NJ) embedded graph reinforcements of Example 4.

Method: Reinforced tubes were prepared as described in Example 2. The ends of a PTFE graft tube and the mesh reinforced end of the tube were sutured together as shown in FIG. 5A.

Figure 9:
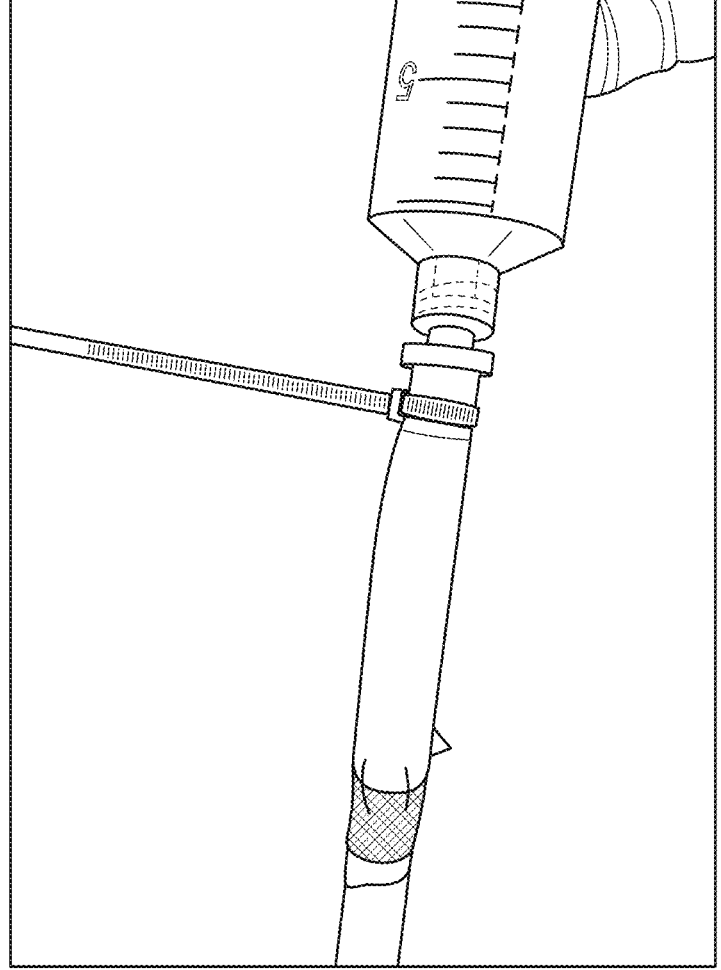
FIG. 9: ePTFE vascular graph experimental apparatus of Example 4, ends were approximated together, sutured with running suture, pulled tight and knotted with a square knot, union sealed with cyanoacrylate glue, and water+India ink was pumped through tube and no leakage observed.
Figure 10A:
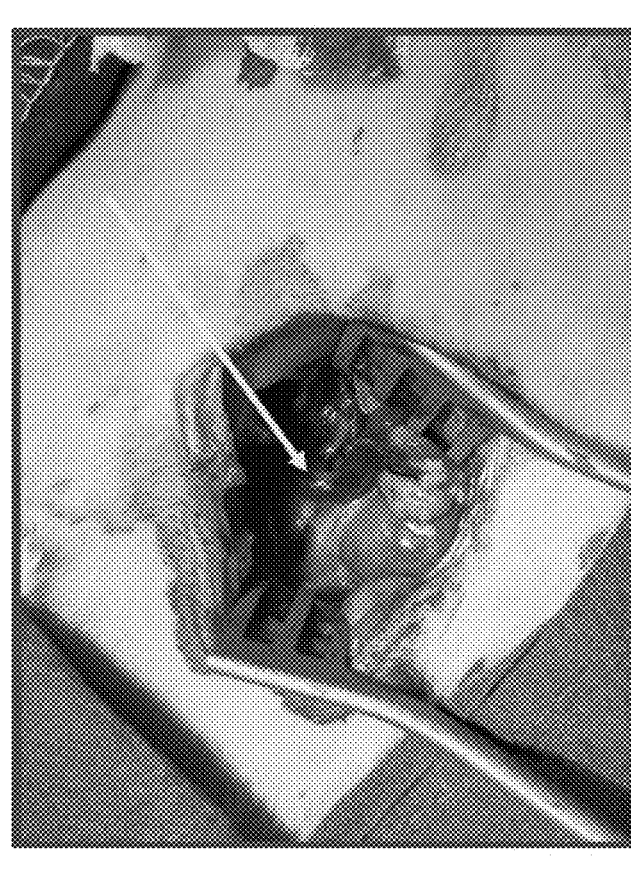
FIGS. 10A-10C: Rabbit PA (pulmonary artery) experimental setup of Example 6.
Figure 10B:
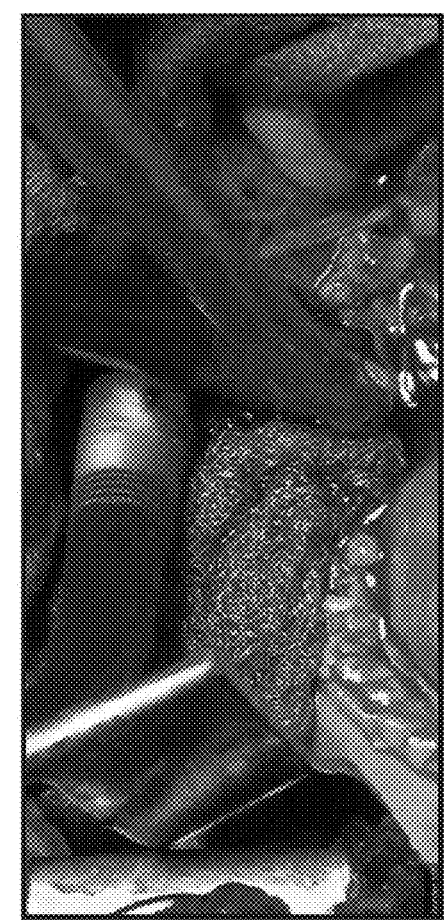
Figure 10C:
Figure 10C:
Figure 11:
FIG. 11: Pig PA defect experimental setup according to Example 10, showing reinforced tube implanted into pig's pulmonary artery (also see FIG. 10A).
Figures 12A, 12B, 12C:
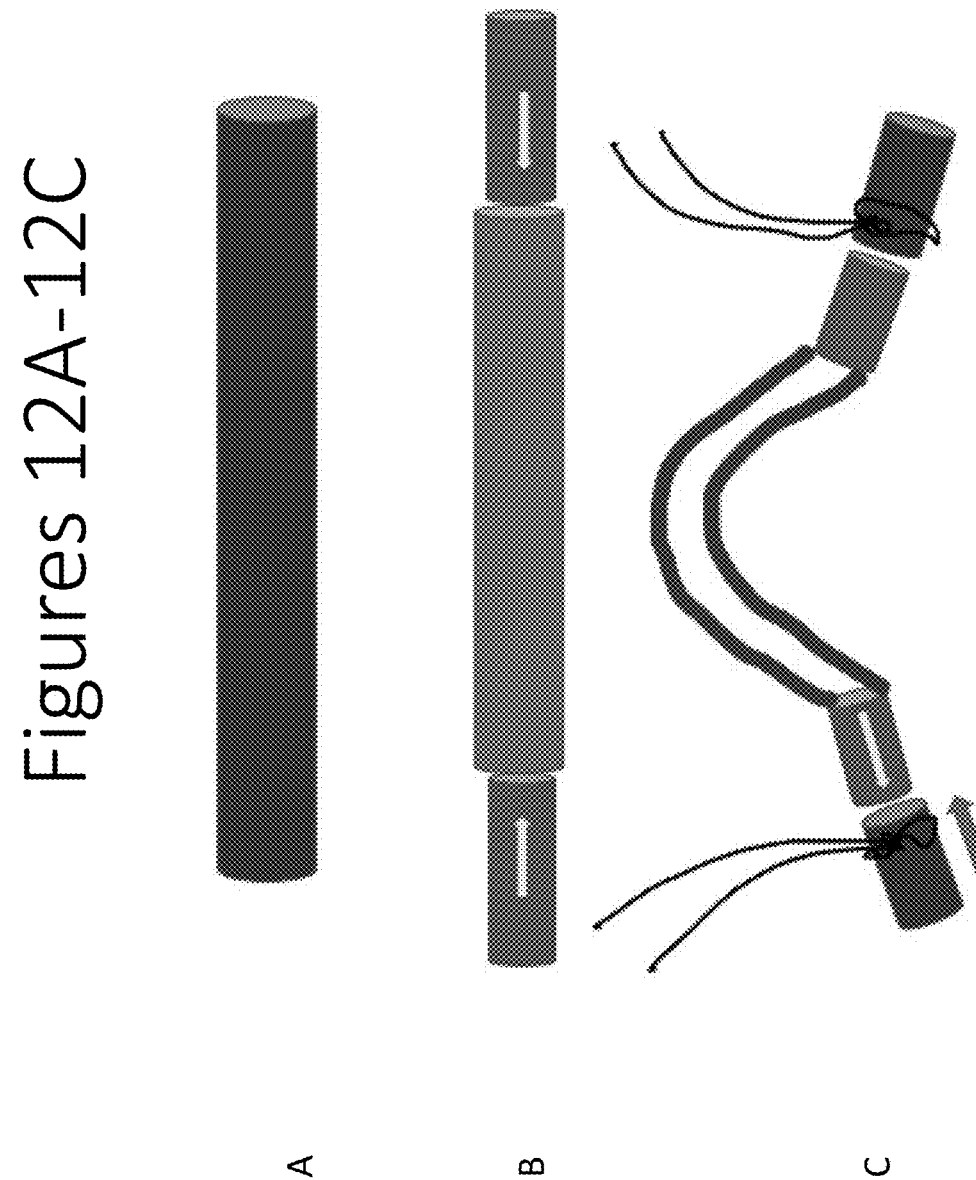
FIGS. 12A-12C: Schematic of PA defect correction.
Figure 13:
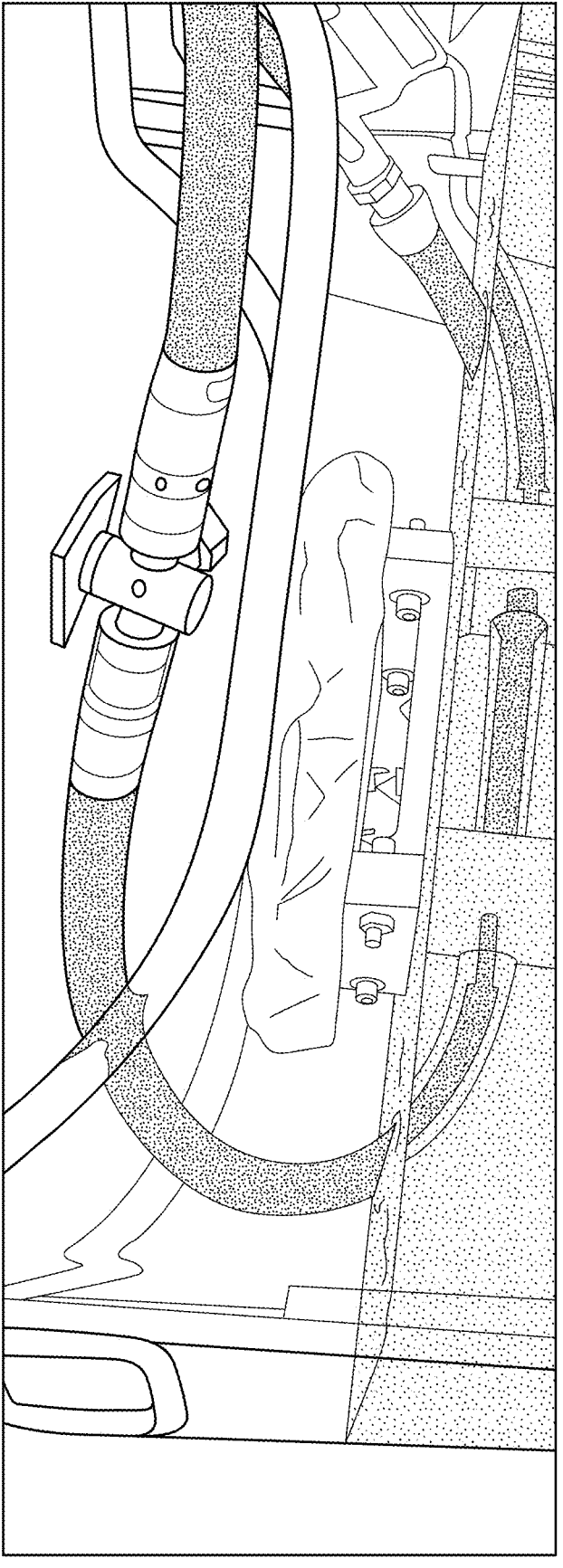
FIG. 13: Experimental apparatus for continuous pumping experiment.
Figure 14:
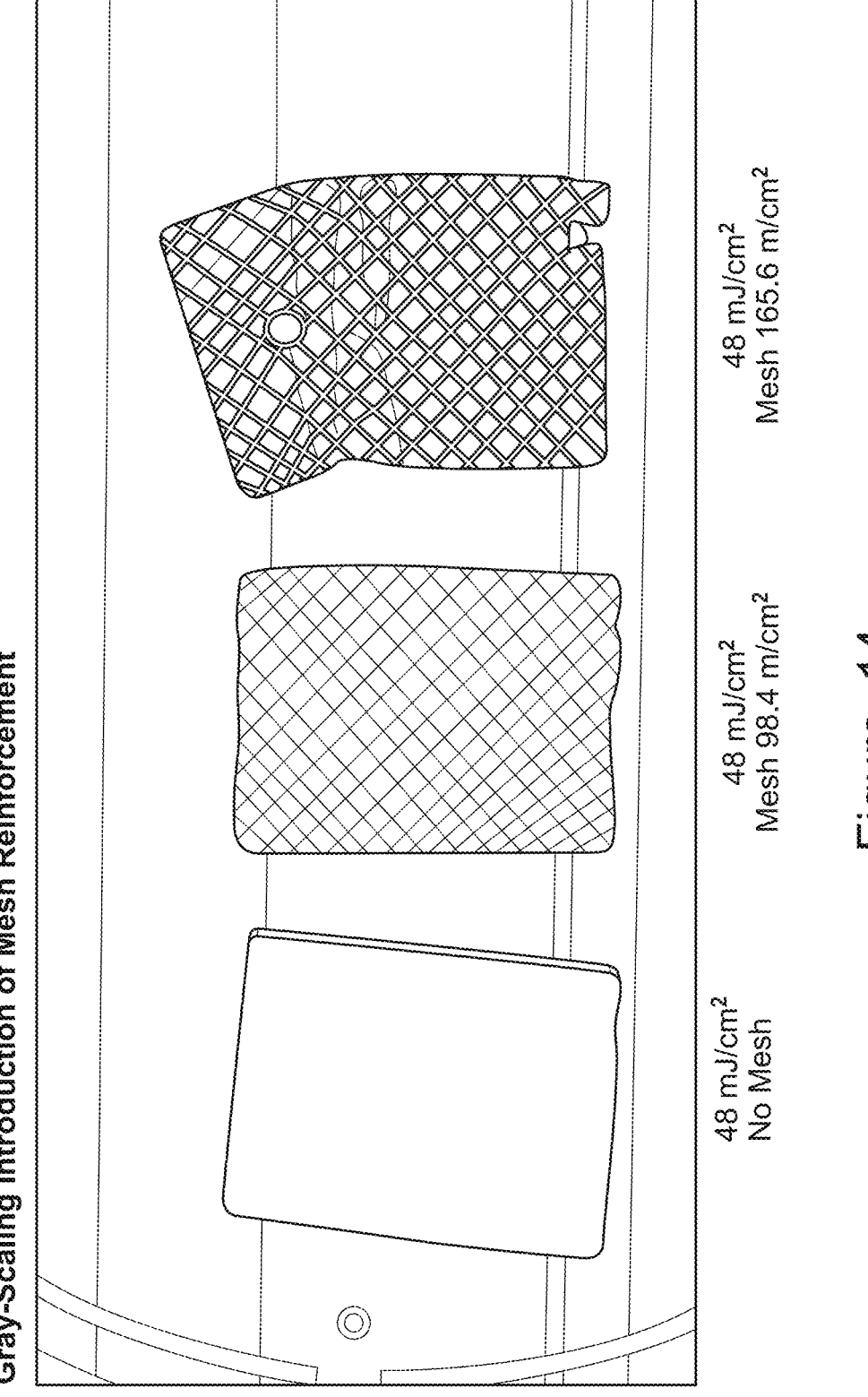
FIG. 14: Introduction of reinforced ends to enhance suturability. Shown are three hydrogel sheets that were printed with varied energy levels. The mesh network that is seen by visual inspection was printed with higher energy than the bulk of the sheet material. In each case the bulk material was printed at 48 mJ/cm2, while the strands of the mesh are higher energy as indicated in the labels. The increased energy regions were controlled by using grayscale to control the exposure in the image.

Results: Water with red ink was injected through the graft as shown in FIG. 9. No leaks were observed. The end of the hydrogel tube was occluded and no leaks at the interface were observed.

Example 5: Embedded Graft Suture Anchor for Use in Porcine (Pig)

The purpose of this experiment was to create a more functional vascular graft for pig model implementation. The goal was to develop a 602N vascular graft augmentation to make printed parts suitable for suturing in animal models.

Figure 4A:
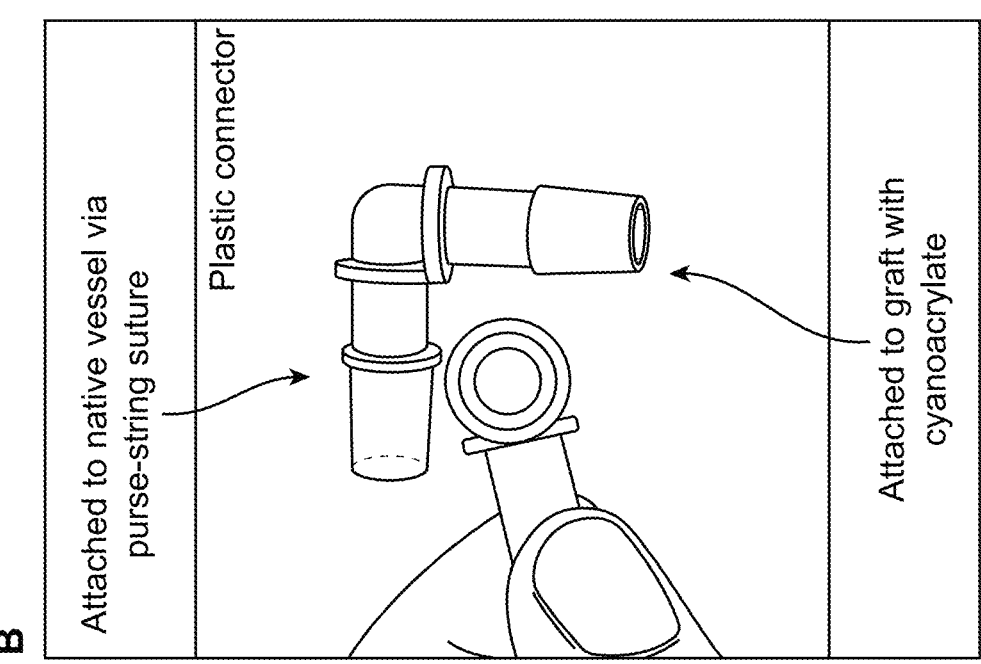
FIGS. 4A-4F: Porcine artery connection discussed in Example 5.
Figure 4B:
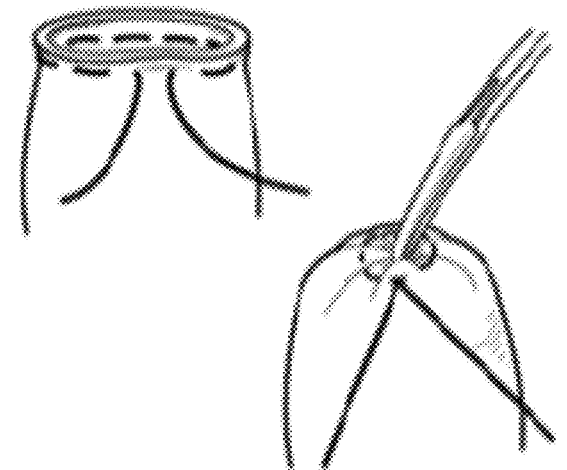

Following the surgeon feedback from the vascular graft tubes made, problems persisted in connecting 602N tubes to native vessels. Previously, hard plastic barb connectors were being attached to the ends of the graft (using cyanoacrylate) and a purse-string suture (FIG. 4A) is tied on the native vessel to tighten it around the connector (FIG. 4B). The cyanoacrylate hardens the hydrogel tubes and makes the ends brittle/unsuitable for long term use, in addition clot formation within the connector has been observed in rabbit models. The development of a more robust interface is necessary.

By embedding surgical mesh anchors within the hydrogel, Applicant eliminates the need for a connector entirely and allows the graft to be directly sutured to native vessels.

Figures 24A, 24B:
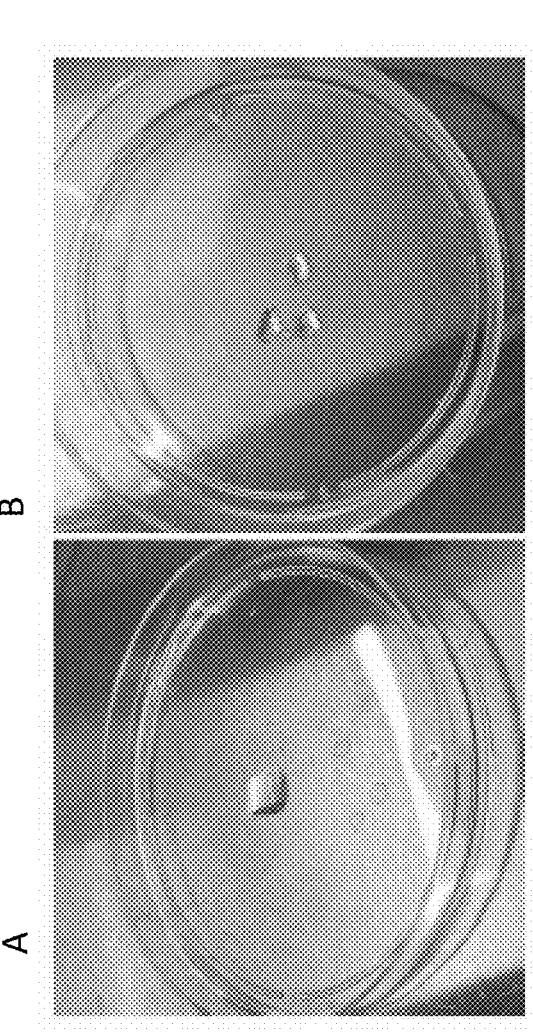
FIG. 24A shows the uncured 602N ink and FIG. 24B shows cured ink.

Materials and Methods: Flashlight: Sunlite 365 nm UV Flashlight (Measured power of 20 mW/cm² at center of glass) Ink used: 602N. To begin, the 365 nm UV flashlight was tested by curing 50 um of 602N in a petri dish. The flashlight was held around 5 cm away from the droplet and turned on for around 10 seconds (FIG. 24A shows the uncured 602N ink and FIG. 24B shows cured ink).

First test samples was created using a sheet of 12 ply medical gauze. Strips of gauze were cut (1×5 cm) and wrapped around end of a 602N graft (5 mm ID 1.5 wall thickness. A small bulb pipet was used to dispense ~1 mL of uncured ink on top of the gauze and was cured with a UV flashlight for around 30 seconds.

Results: Initial results of the 12 ply gauze anchor test were very positive. The loose threads caused the gauze anchor to bunch up/fray in some areas prior to curing the ink. Despite the messy outward appearance, the gauze was able to distribute the stress of the suture across the surface and allowed the graft to successfully hold a suture without tearing. The supported area was able to be pierced by a suture needle and showed no signs of tearing or fracturing at moderate levels of tension.

Initial reinforced grafts created with 1 layer 12 ply gauze (2 cm section on each end). Tested with closed loop suture worked well with no fractures/cracks observed in the graft. Reinforced gauze graft was able to withstand tension without tearing or breaking. Additional reinforced grafts were made with the same technique using Vicryl surgical mesh and sent to a surgical team for evaluation and feedback. Supports were cured into structure with approximately 2 mL ink in a 1 mm thick layer, ink was cured for approximately 40 sec per/side.

Figures 4C, 4D, 4E, 4F:
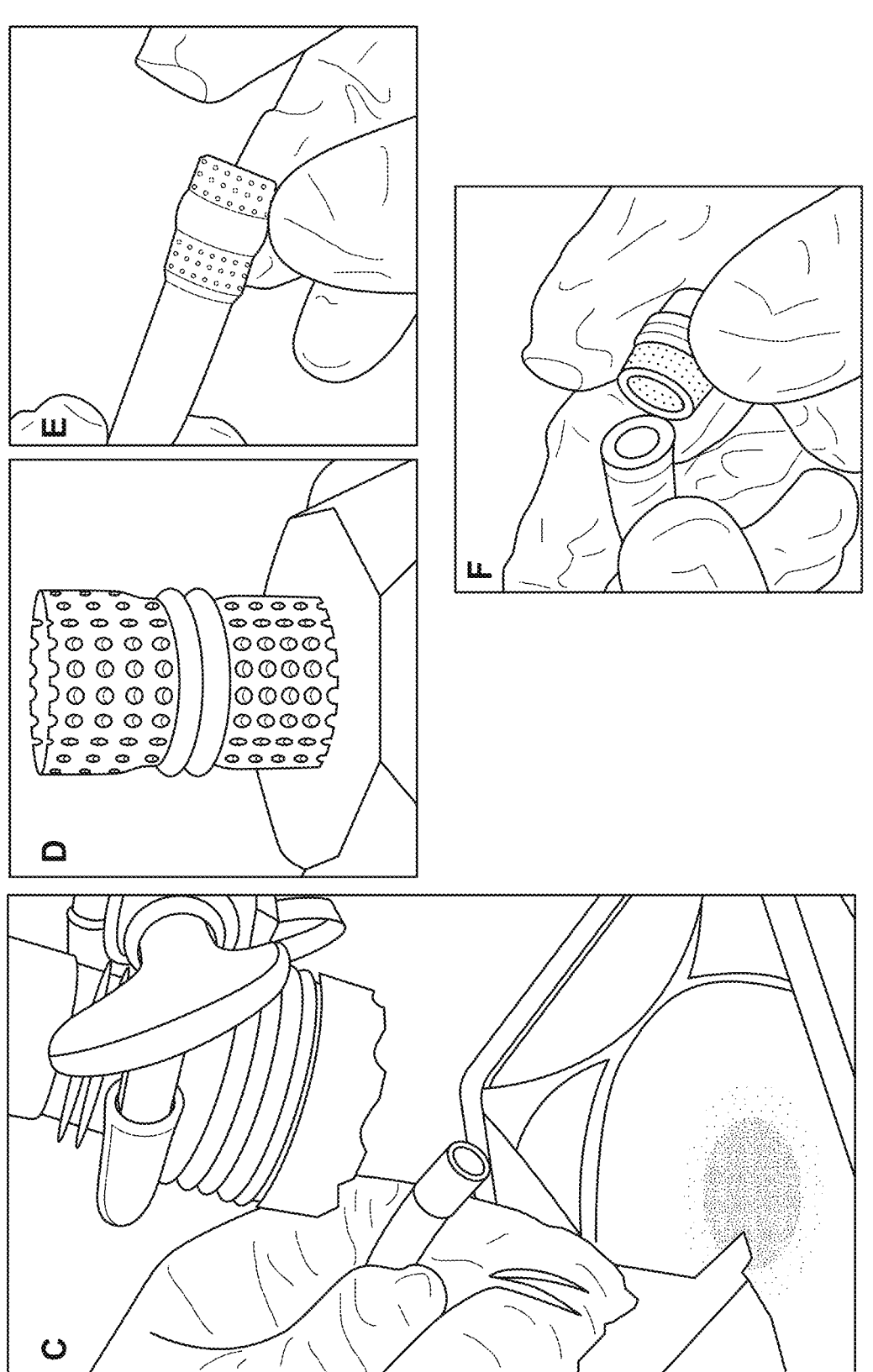

Additional supports were tested by printing Formlab Elastic v1 Resin printed anchors and securing them to ends with 602N and UV flashlight. Anchors were designed to replace plastic connectors and allow for purse-string suture connection. Net/mesh ends designed to secure anchor to graft once ink is cured and a grooved band was designed to seat purse-string suture and withstand compressive force. Mixed results after implementation, the saw-like edge (FIG. 4D) caused the graft to cut through the newly cured ink and tear away from the graft (FIG. 4F).

Example 6: Pumping Experiment

Figure 15A:
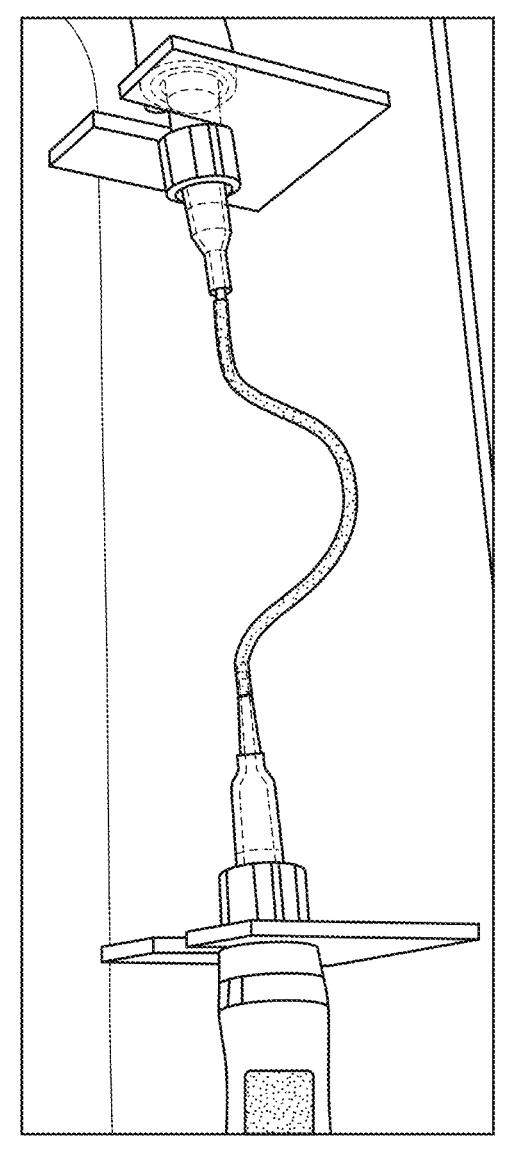
FIGS. 15A-15B: Cuff or sleeve experimental apparatus according to Example 6.
Figure 15B:
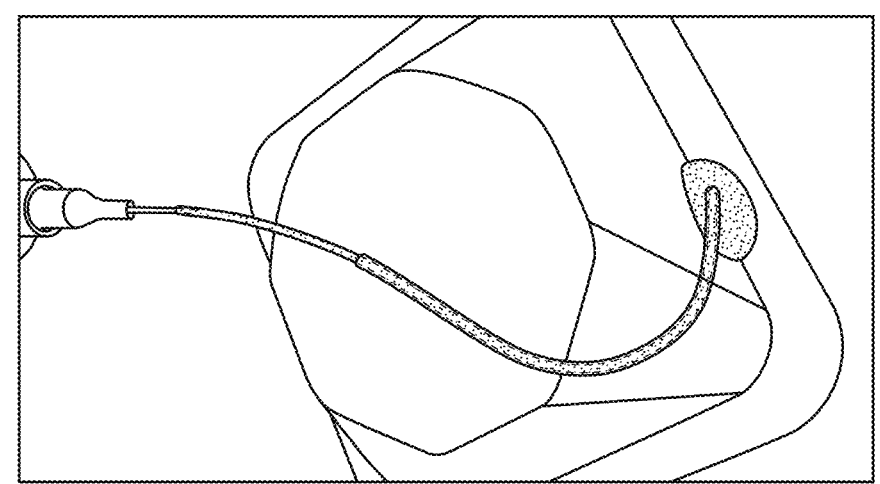
Figure 16:
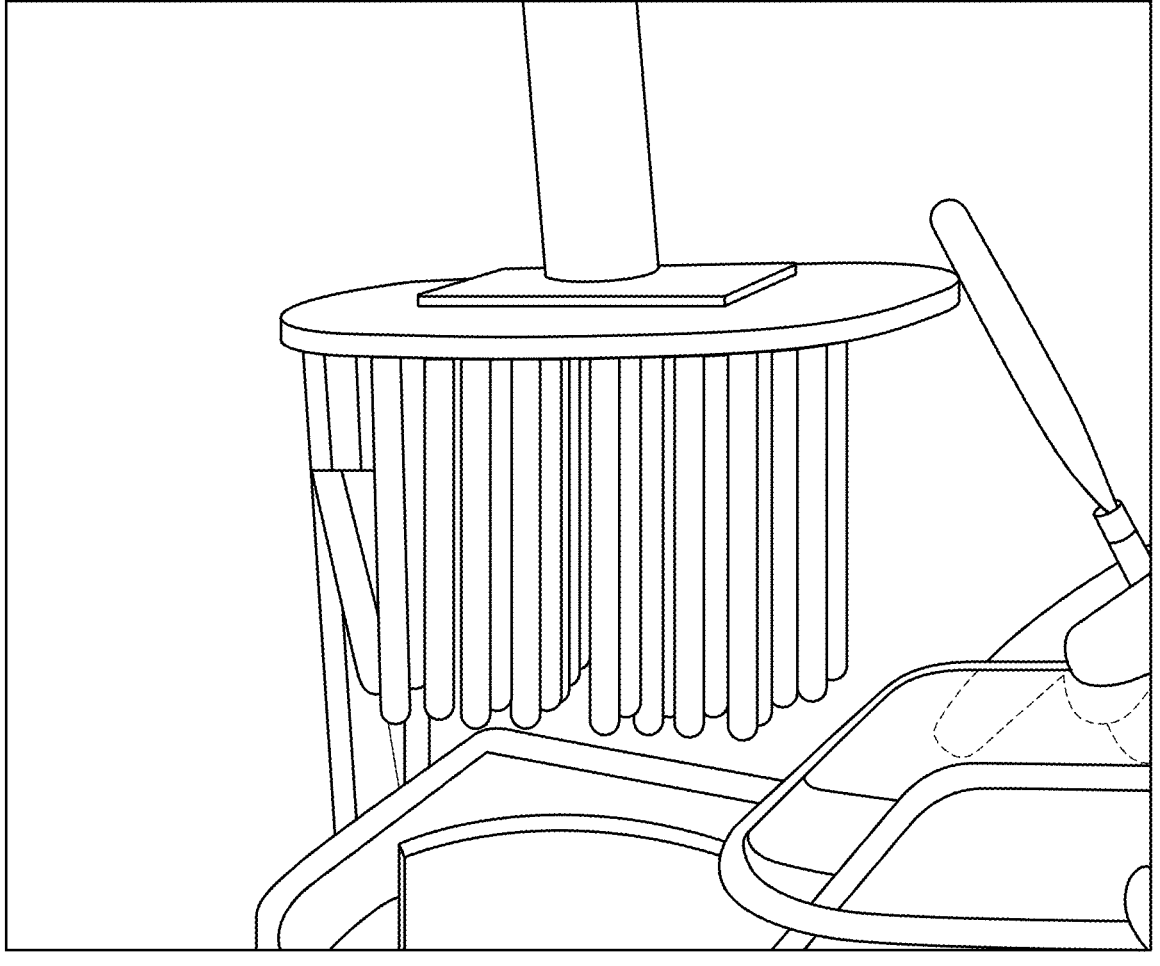
FIG. 16: 3D printed hydrogel vessels.
Figures 17A, 17B:
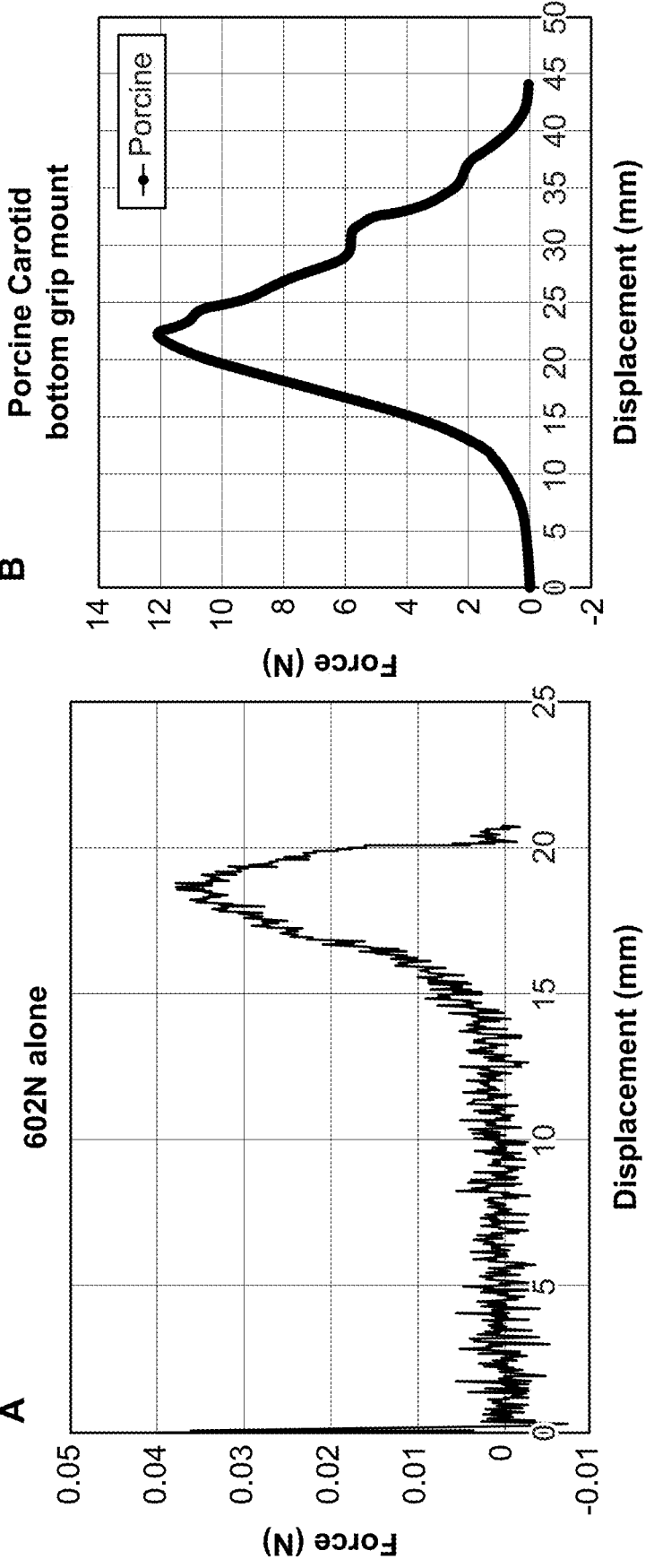
FIGS. 17A-17C: Experimental results for force pull out experiments for 17A (602 tube sample), 17B (porcine carotid artery tissue alone), and 17C (fore pull out for 602N tube and carotid artery)
Figure 17C:
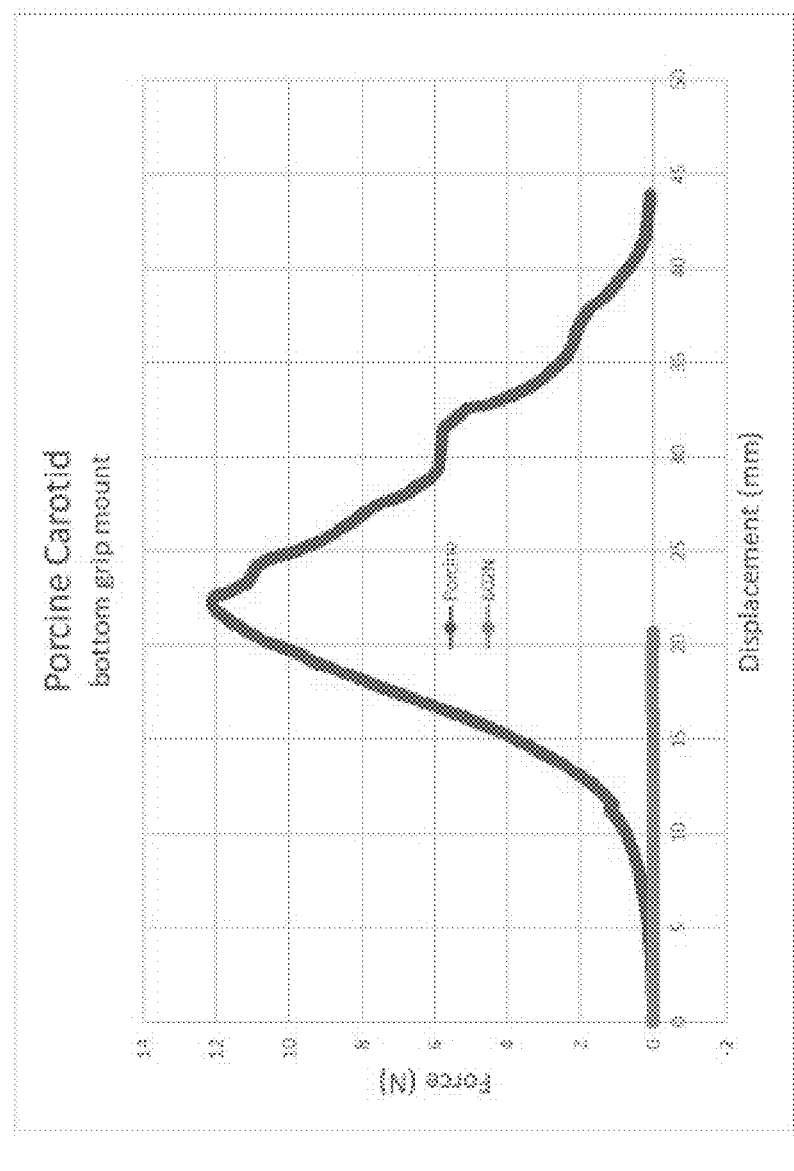
Figure 18A:
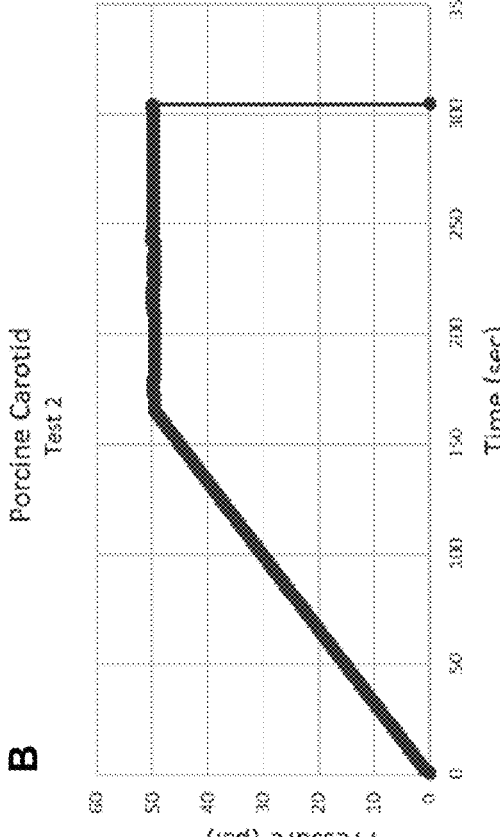
FIGS. 18A-18B: Burst/cycling experiment showing the sample connected to tubing for burst test B shows the pressure increasing over time until our maximum pressure of the system was reached. The sample never failed.
Figure 18B:
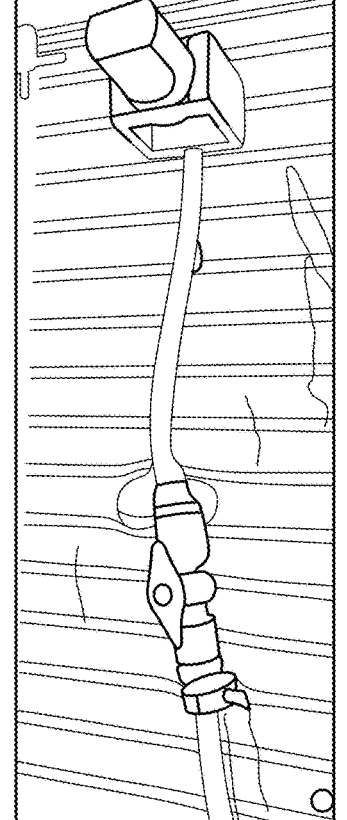
Figures 19A, 19B:
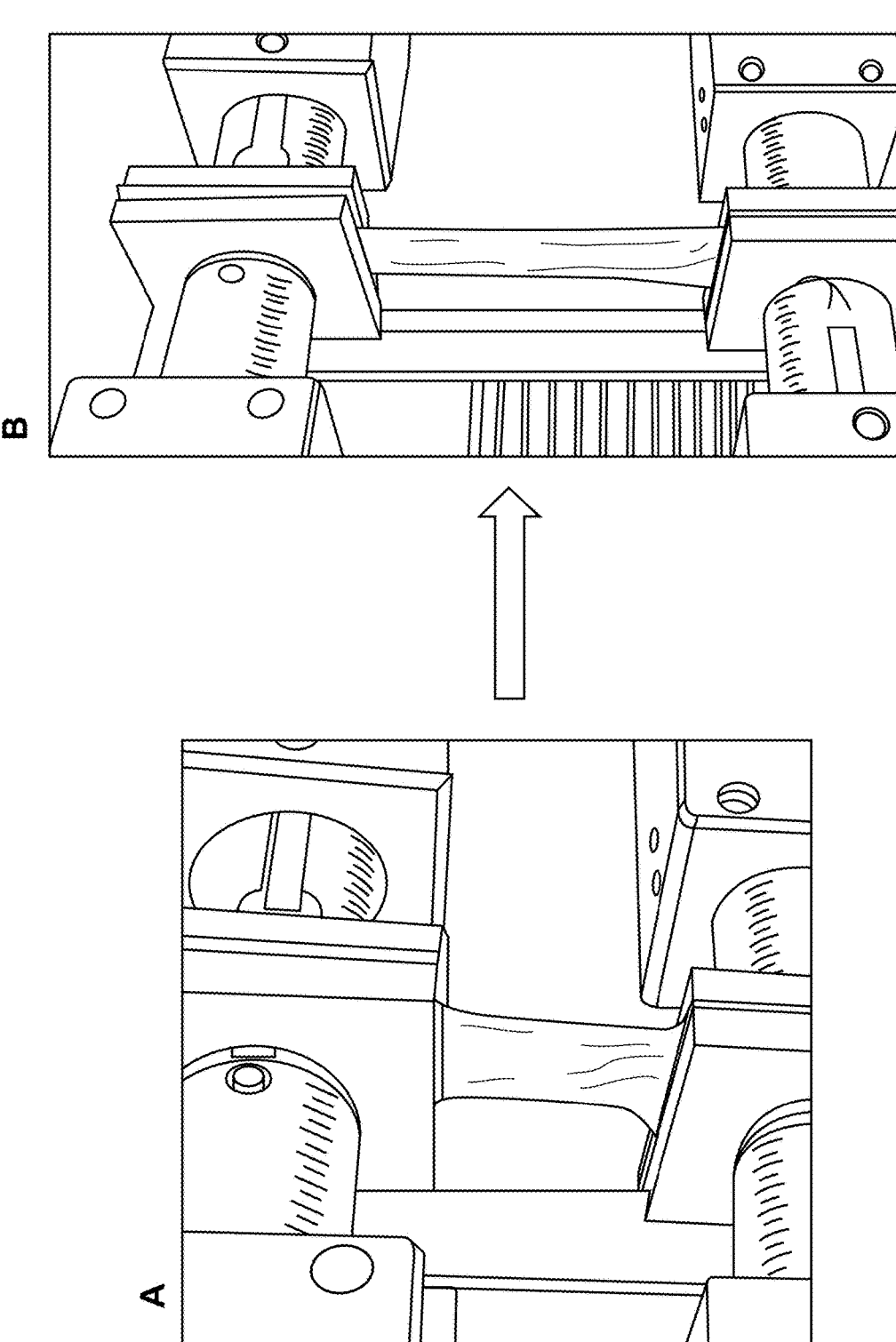
FIGS. 19A-19B: Apparatus for tensile testing experiment with specimen (FIG. 19A) and specimen being pulled to failure (FIG. 19B) according to Example 7.

An Ismatec Reglo ICC from Cole Parmer, Barrington, IL was used with tygon tubing, leuer locks, regarding assembly of apparatus of FIG. 15 Results: After pumping all night with no leaks pressure was increased until failure point. Rupture occurred: 0.5 mL per stroke/~80 strokes/minute=40 mL/min Did not rip tube luer lock separated from mounting interface. Final dimensions: 2 mm OD, 1.5 ID.

Example 7: Tensile Testing

Figures 20A, 20B:
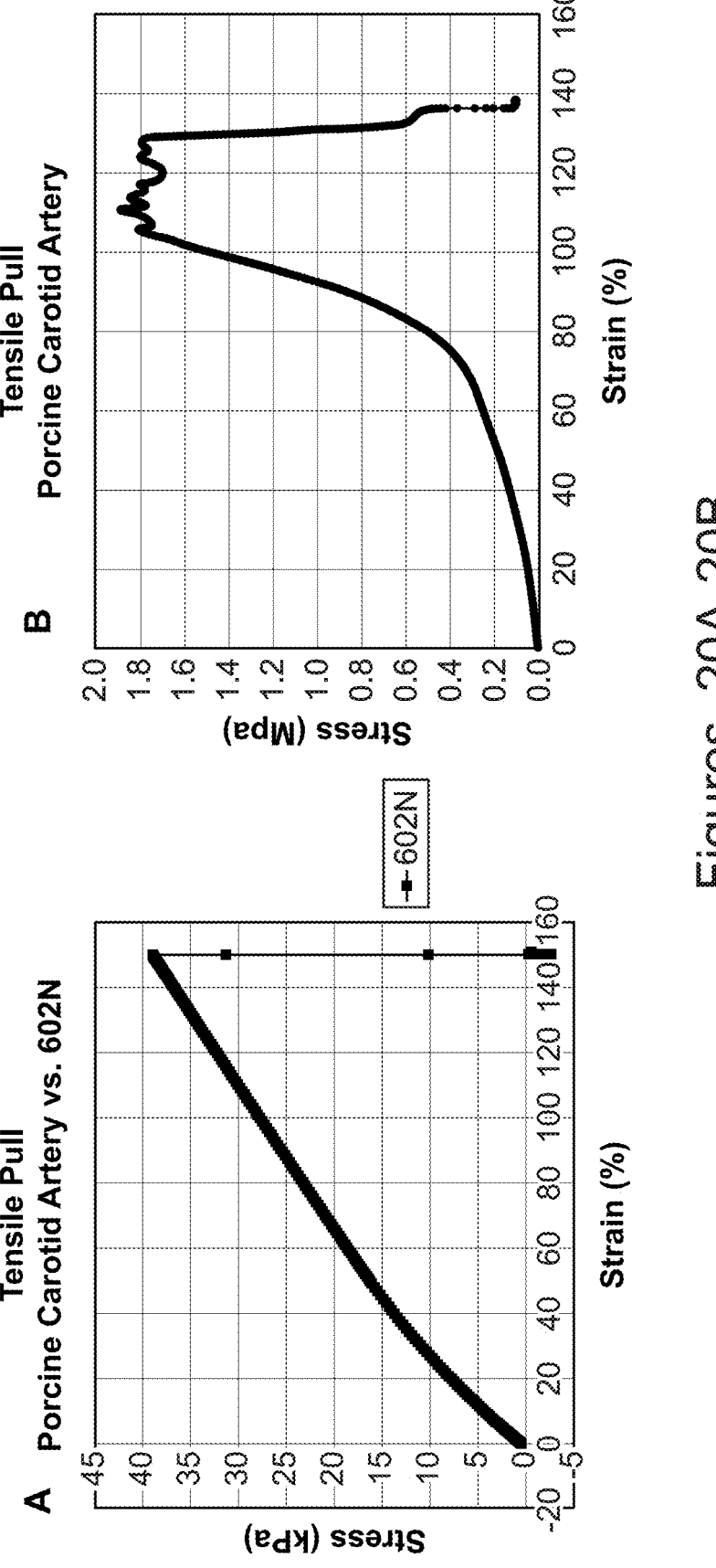
FIGS. 20A-20C.
Figure 20C:
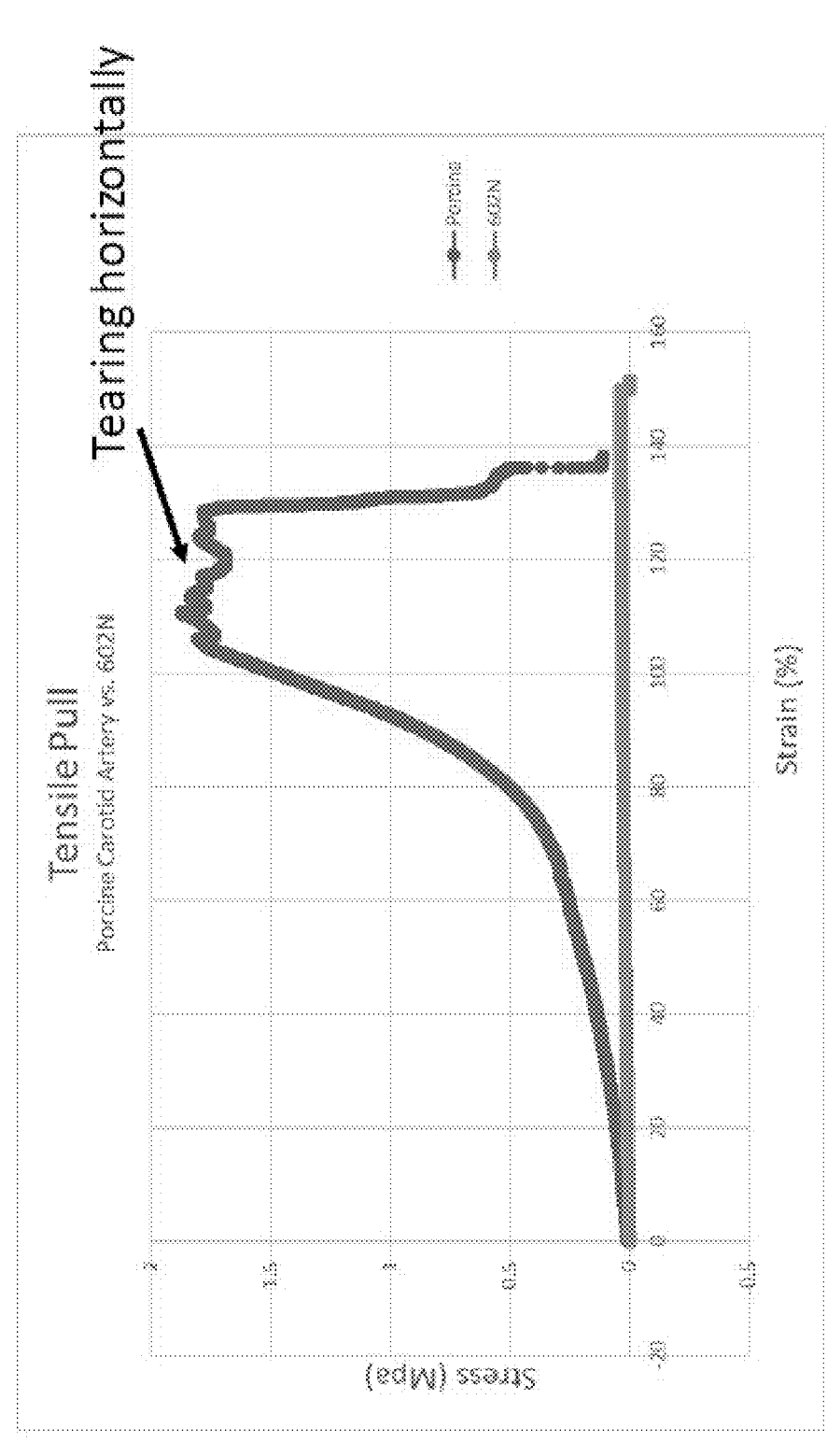
Figures 21A, 21B, 21C:
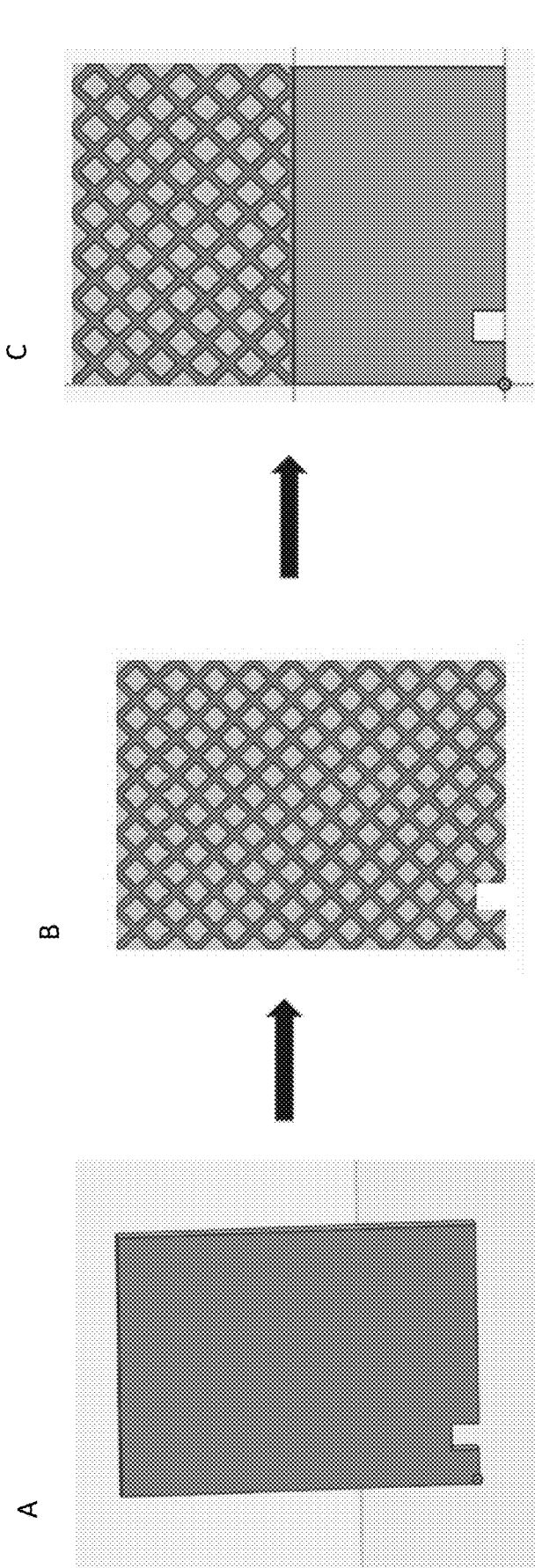
FIGS. 21A-21C: a technical drawing (CAD drawing) of the device of FIG. 14.
Figure 22:
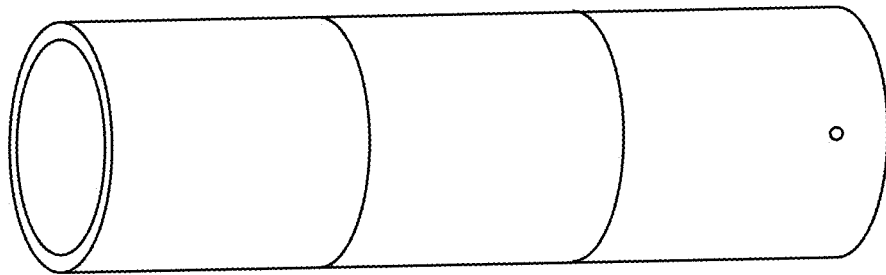
FIG. 22: Embedded pattern at the tube ends to increase suturability.
Figures 23A, 23B:
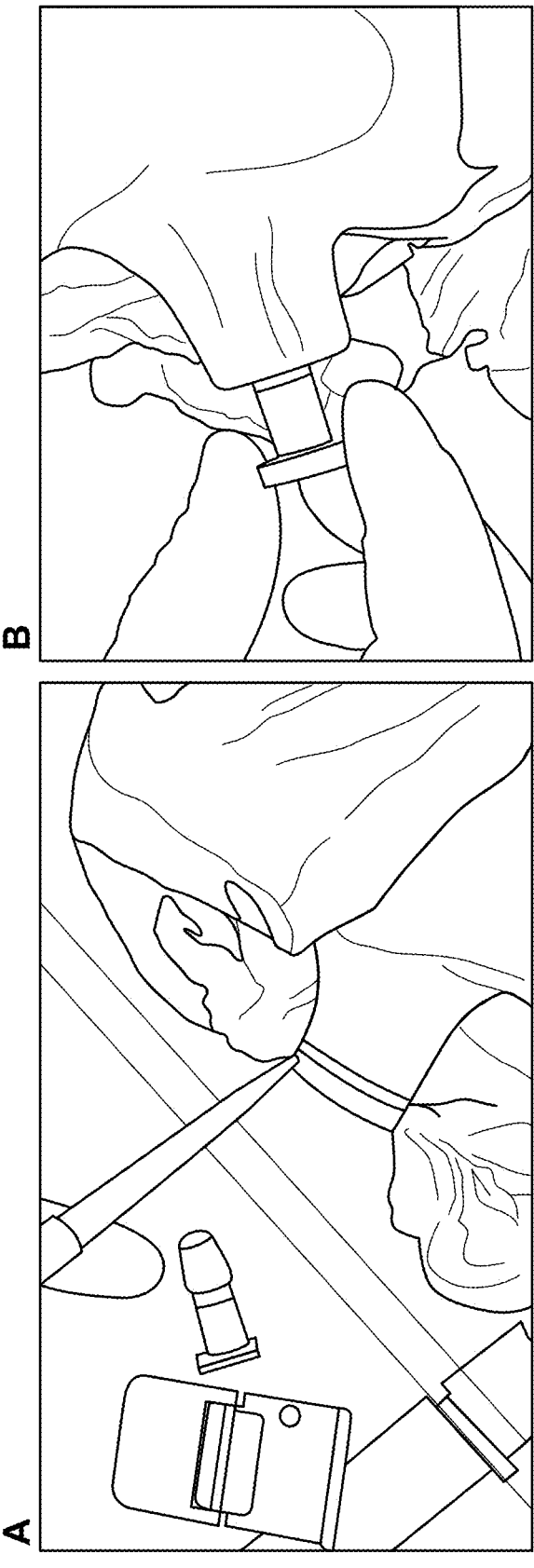
FIGS. 23A-23B: Utilizing the reinforced process to patch a crack observed in a leaking conduit (FIG. 23A). Reinforcing lung lobe scaffold hydrogels with mesh (FIG. 23B). The procedure was performed as follows: 1. Crack in object is identified. 2. Uncured ink is applied via pippete onto cracked surface 3. Light of the appropriate wavelength is applied with a flashlight for 2-4 seconds at a distance of approximately 3 inches from surface 4. Object is retested and if crack persists, procedure is repeated.

Single rectangular portion of artery recovered from burst test mounting apparatus was pulled to failure at the same rate as previous dog-bone samples. Converted all data to MPa as shown in FIG. 20A-C.

Example 8: Suture Pull Out Test

Method:
a) Using an apparatus and shown in FIGS. 3A-3D, before starting testing, select the grip faces to be used and press fit them onto the grips. The faces have a 5 mm bite distance channel.
b) Membranes should be stored in DPBS, without Ca, without Mg for a minimum of 2 hours at 37° C. prior to testing.

c) Remove membrane from buffer, gently blot bottom edge against a Kimwipe. Align the top edge of the membrane with the top edge of the grip jig.
   Ensure that the base layers are at the bottom as indicated by the notch in the membrane.
   Ensure that the membrane is contacting the sandpaper surface for gripping.
   Tighten the grips until finger tight. Do not over-tighten as the membrane will squeeze up above the top of the grip face mounts.
d) Insert a fresh suture while making contact between the needle and the bottom of suture channel. Carefully pull the suture through the membrane by grasping the needle from the exit side and gently pulling through.
e) Align the suture ends, secure together on a piece of tape perpendicular to the tape edge, then press the tape against the face of one of the upper grips. Center the suture edges on the upper grip face.
f) Tighten grips until firmly closed.
g) Use jog feature to remove the majority of slack from the suture lengths. Leave a slight amount of bend to the suture threads. The final slack will be removed using the pre-load feature in the method.
h) Zero displacement and zero load
i) Start test

Example 9: Pulmonary Artery in Porcine Repaired with Reinforced Tubes

Purpose: To evaluate the ability of artificial pulmonary artery to support the physiological pressure induced by blood flow, animal models are needed. The pig model provides a reproduction in term of similar size of human pulmonary system and is well-known for its application in several translational research.

Methods:
1. The pig will be sedated thirty minutes before the surgery with an intramuscular injection of Ketamine 20 mg/kg, Acepromazine 1.1 mg/kg and Atropine 0.04 mg/kg.
2. The animal will be placed on the surgery table. ECG probes, rectal probe thermometer and pulse oximeter will be placed on the animal to monitor the heart rate, body temperature and saturation throughout the surgery.
3. The anesthesia will be induced by intravenous slow bolus injection of Propofol at 0.14 mg/kg.
4. A propofol infusion at 1.4 mL/min at the dose of 0.4 mg/kg/min will be started to maintain the anesthesia for the entire surgery. An intramuscular injection of Meloxicam (0.4 mg/kg) will be administrated for analgesia. The depth of anesthesia will be monitored throughout the surgery (heart rate, eyes reflex, jaw tone) and the dose of propofol will be increased if needed.
5. A sustained intravenous infusion of Ringer's solution will be administrated through for the entire surgery (50-60 drops/min).
6. The pig will be installed in a prone position to inject spray of lidocaine (10 mg/mL) on the arytenoids.
7. Five minutes after the lidocaine spray, the pig will be intubated with a 6.5 endotracheal tube and immediately ventilated with 100% oxygen using an Ohmeda 7800 ventilator (tidal volume of 7 mL/kg and respiratory rate of 25-28 breath/min).
8. The pig will be placed on his right side in preparation for the thoracotomy.

9. A second intramuscular injection of Meloxicam (0.2 mg/kg) will be administrated and a subcutaneous injection of bupivacaine 1 mg/kg will be administrated at the opening site.

10. An incision of approximately 15 cm will be made through the right second intercostal space.

11. A dissection will be done to expose the pulmonary artery. A particular attention will be paid to avoid the vagus nerve.

12. The vena cava will be moved away with forceps to give enough space to implant the artificial vessel.

13. The pulmonary artery will be clamped to stop the blood from passing through. An incomplete incision will be done on the pulmonary artery to introduce the artificial vessel connectors.

14. The sample grafts will be inserted into the pulmonary artery through the incision and tightened in place with sutures. The clamps will be removed from the artery to allow the blood flow to pass through the artificial pulmonary artery.

What is claimed is:

1. A method of preparing a reinforced structure, comprising contacting a mesh immersed in an uncured photocurable bioink with a first hollow tube, an outer wall of the hollow tube being continuous, and irradiating the mesh immersed in the uncured photocurable bioink in contact with the hollow tube, thereby adhering the mesh to the hollow tube via a hydrogel formed from the photocurable bioink to form a tube reinforced by the mesh.

2. The method of claim 1, wherein the mesh has a thickness of about 0.1 μm to about 2 mm.

3. The method of claim 1, wherein the mesh spirals around a sublength of the hollow tube.

4. The method of claim 1, wherein the contacting comprises contacting an outside surface of the hollow tube with the mesh.

5. The method of claim 1, wherein the contacting and the irradiating are repeated more than once to form two or more layers of the mesh.

6. The method of claim 5, wherein the two or more layers are stacked.

7. The method of claim 1, wherein the photocurable ink comprises a photoinitiator and/or dye that reacts and/or absorbs light with a wavelength of about 100 to about 400 nm.

8. The method of claim 1, wherein the reinforced tube has a burst pressure of 1,000 mmHg or greater.

9. The method of claim 1, wherein the contacting comprises suturing the reinforced tube to a second hollow tube.

10. The method of claim 9, wherein the reinforced tube has a suture pullout force of a site of the suturing 2.5 times to 15 times greater than a non-reinforced hollow tube.

11. The method of claim 9, wherein the reinforced tube has a suture retention of 1.5 N or greater.

12. The method of claim 1, wherein the first hollow tube comprises a first subtube, a second subtube and a joint connecting the first subtube and the second subtube, wherein the contacting comprises contacting the mesh with the joint of the first hollow tube.

13. The method of claim 1, wherein the contacting comprises contacting the hollow tube with the mesh at a sublength constituting from 0.1% to 50% of the hollow tube.

14. The method of claim 13, wherein the sublength is from 1 mm to 2.5 cm.

15. The method of claim 1, wherein the reinforced tube is a vascular graft.

16. A method of treating ischemic disease in a subject in need thereof, the method comprising implanting the reinforced tube produced by the method of claim 1.

* * * * *